US010329589B2

(12) United States Patent
Yu et al.

(10) Patent No.: US 10,329,589 B2
(45) Date of Patent: Jun. 25, 2019

(54) METHOD FOR PREPARING SUGAR, BIOETHANOL OR MICROBIAL METABOLITE FROM LIGNOCELLULOSIC BIOMASS

(71) Applicant: Korea Research institute of Chemical Technology, Daejeon (KR)

(72) Inventors: Ju Hyun Yu, Daejeon (KR); Chan Duck Jung, Daejeon (KR); In Yong Eom, Daejeon (KR); Seung Hwan Lee, Daejeon (KR); Kyung Sik Hong, Daejeon (KR); In-Chul Kim, Daejeon (KR); Jong Geon Jegal, Daejeon (KR); Bong Keun Song, Daejeon (KR)

(73) Assignee: Korea Research Institute of Chemical Technology, Daejon (KR)

( * ) Notice: Subject to any disclaimer, the term of this patent is extended or adjusted under 35 U.S.C. 154(b) by 0 days.

(21) Appl. No.: 14/991,209

(22) PCT Filed: Jun. 9, 2014

(86) PCT No.: PCT/KR2014/005045
§ 371 (c)(1),
(2) Date: Jan. 8, 2016

(87) PCT Pub. No.: WO2015/005589
PCT Pub. Date: Jan. 15, 2015

(65) Prior Publication Data
US 2016/0298142 A1    Oct. 13, 2016

(30) Foreign Application Priority Data

Jul. 9, 2013    (KR) .................. 10-2013-0080477
Jul. 12, 2013   (KR) .................. 10-2013-0082290
Aug. 23, 2013   (KR) .................. 10-2013-0100559
Jan. 13, 2014   (KR) .................. 10-2014-0003775

(51) Int. Cl.
| *C07H 1/06*   | (2006.01) |
| *C12P 7/06*   | (2006.01) |
| *C07H 3/02*   | (2006.01) |
| *C12P 7/10*   | (2006.01) |
| *C12P 7/14*   | (2006.01) |
| *C12P 19/14*  | (2006.01) |
| *C13K 1/02*   | (2006.01) |
| *C12P 7/56*   | (2006.01) |
| *C12P 19/56*  | (2006.01) |
| *C12P 19/02*  | (2006.01) |

(52) U.S. Cl.
CPC .................. *C12P 7/14* (2013.01); *C07H 1/06* (2013.01); *C07H 3/02* (2013.01); *C12P 7/065* (2013.01); *C12P 7/10* (2013.01); *C12P 7/56* (2013.01); *C12P 19/02* (2013.01); *C12P 19/14* (2013.01); *C12P 19/56* (2013.01); *C13K 1/02* (2013.01); *C12P 2201/00* (2013.01); *Y02E 50/16* (2013.01); *Y02E 50/17* (2013.01)

(58) Field of Classification Search
CPC .... C12P 7/14; C12P 7/065; C12P 7/10; C12P 19/14; C12P 2201/00; C07H 3/02; C07H 1/06; Y02E 50/16; Y02E 50/17
See application file for complete search history.

(56) References Cited

U.S. PATENT DOCUMENTS

2010/0285574 A1    11/2010    Genta et al.
2013/0288312 A1    10/2013    Yu et al.

FOREIGN PATENT DOCUMENTS

| JP | 2009183805 A    | 8/2009 |
| KR | 1020110040367 A | 4/2011 |
| KR | 20140005067 A   | 1/2014 |

OTHER PUBLICATIONS

Taherzadeh et al., Int. J. Mol. Sci., 2008, vol. 9, p. 1621-1651.*
Mosier et al., Bioresource Technology, 2005, vol. 96, p. 673-686.*
Kim et al., Bioresource Technology, 2005, vol. 96, p. 1994-2006.*
PCT International Search Report for PCT/KR2014/005045 dated Dec. 5, 2014.
PCT Written Opinion for PCT/KR2014/005045 dated Dec. 5, 2014.

* cited by examiner

*Primary Examiner* — Kade Ariani
(74) *Attorney, Agent, or Firm* — Faegre Baker Daniels LLP

(57) ABSTRACT

The present invention relates to a method for preparing bioethanol from lignocellulosic biomass. The method of the present invention is capable of: minimizing the impurity content of an enzymatic saccharification raw material, by extracting biomass using hot water, before pretreatment, and removing extractable substances such as inorganic salts; suppressing, to the greatest extent, the production of over-decomposition products of sugar, by pretreating the biomass, from which the hot water extractable substances have been removed, in a condition for maximizing xylan yield; preparing fermentable sugar at a low cost, without washing a pretreated solid obtained from subsequent solid-liquid separation, but by only concentrating a sugar solution obtained after enzymatic saccharification, using a separation film; and preparing bioethanol therefrom in high yield.

8 Claims, 1 Drawing Sheet

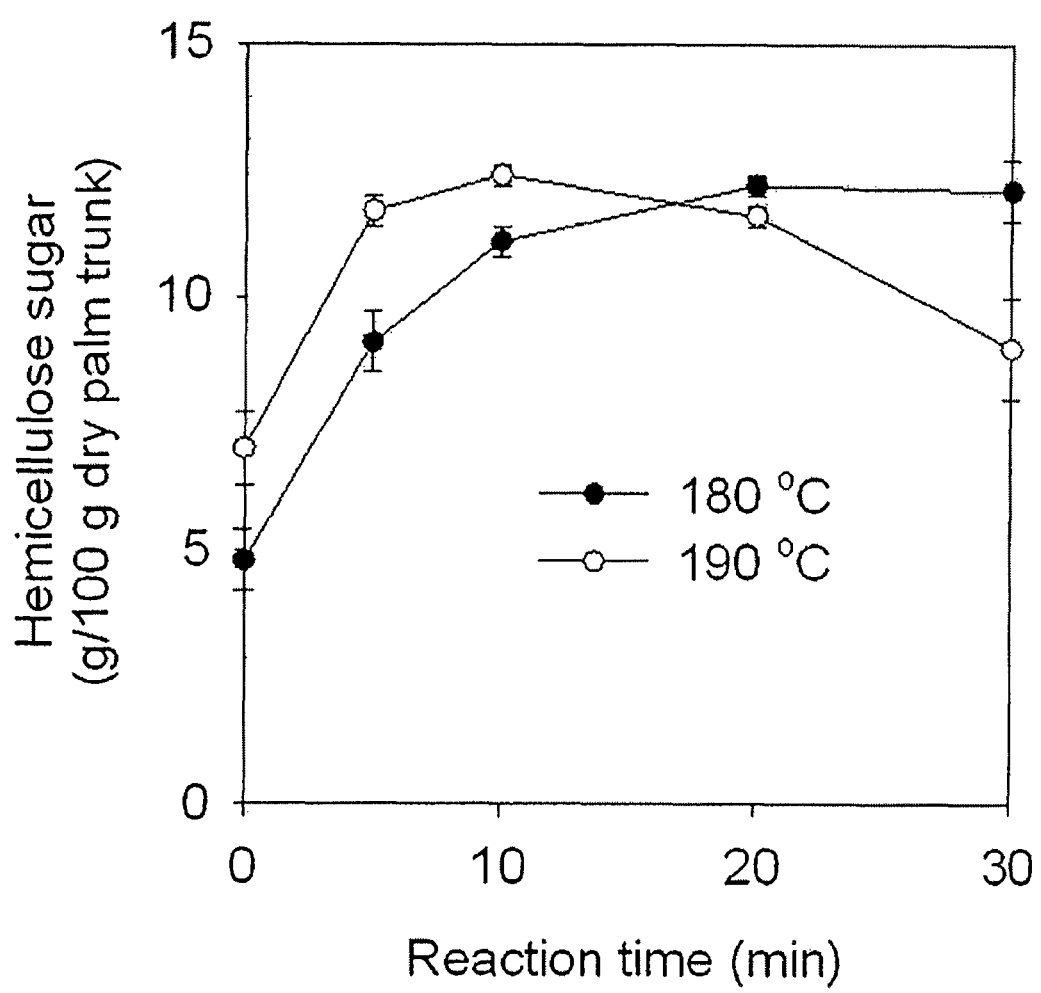

METHOD FOR PREPARING SUGAR, BIOETHANOL OR MICROBIAL METABOLITE FROM LIGNOCELLULOSIC BIOMASS

FIELD OF THE INVENTION

The present disclosure relates to a method for producing bioethanol from lignocellulosic biomass, and more particularly, to a method for producing bioethanol which obtains a high concentration of fermentable sugar from lignocellulosic biomass and produces bioethanol through fermentation.

The present disclosure relates to a method for producing fermentable sugar in which fermentable sugar is produced from lignocellulosic biomass as a raw material and can be used for microbial fermentation.

The present disclosure relates to a method for producing fermentable sugar in which fermentable sugar is produced from lignocellulosic biomass as a raw material and significantly reduces in toxicity toward industrial microbes while containing acetic acid.

The present disclosure relates to a method for producing microbial metabolite such as bioethanol or lactic acid from lignocellulosic biomass containing starch at high yields.

The present disclosure relates to a method for preparing a sugar solution using a separation membrane, and more particularly, to a method for preparing a refined sugar solution with a polyamide nanofiltration membrane which is modified to reduce surface charge, thereby, an aqueous sugar solution is filtered using the modified polyamide nanofiltration membrane to remove microbial inhibitors, yielding a refined sugar solution.

BACKGROUND

Recently, to deal with exhaustion of fossil fuel and global warming caused by greenhouse gases all over the world, many research and development has been made to produce fuels for transportation and industrial chemicals from renewable biomass. Particularly, bioethanol used as a biofuel is produced by obtaining sugar from biomass, followed by fermentation.

Biomass that is regarded as being reproduced indefinitely so long as the sunlight exists, includes lignocellulosic biomass mainly including plants on the ground and algal biomass mainly including green algae growing in the water. One of the structural components of biomass, cellulose, is the most abundant material on the Earth and occupies 20% to 50% of biomass, and is a product of condensation polymerization from glucose which is the main source of carbon and energy for fermentation strains. Many research and development is being actively made to produce glucose from cellulose with high quantity and quality.

However, in addition to cellulose, lignocellulosic biomass includes hemicellulose (about 15 to 35%) that is susceptible to acid-catalytic hydrolysis and overdegradation, and lignin (about 10 to 30%) difficult to be broken down into monomers having a particular functional group due to its complex structure. Besides, lignocellulosic biomass contains materials that can be extracted with water, such as, for example, water-soluble starch, free sugar, protein, lipid, pectin, tannin, a variety of alkaloids, organic acids and a variety of inorganic salts, and generally, their amounts in herbaceous biomass are large, for example, 20 to 30%, and their amounts in woody biomass are a bit small, for example, 5 to 20% (Michael E. Himmel (2009) Biomass recalcitrance, Blackwell Publishing; Run-Cang Sun (2010) Cereal Straw as a Resource for Sustainable Biomaterials and Biofuels, Elsevier).

Among the extractable materials of lignocellulosic biomass, starch or free sugar can be used in producing fermentable sugar, but materials other than starch or free sugar act as impurities in fermentable sugar and become a factor that causes the sugar yield to reduce in the production of fermentable sugar, so they need to be recovered or removed.

Korean Patent Publication No. 2011-0040367 discloses an apparatus in which as one process of continuous fractionation of biomass, hot water is fed into a reaction tank in which contains biomass, and after stirring for a predetermined time, a liquid is discharged using stream pressure. The above invention was intended to enable fractionation of hot water extractable materials by the apparatus, but liquid discharge through a valve under high pressure is not easy, and due to a tunneling phenomenon within the contents during discharging, even though extraction and recovery is repeated through a valve, the total recovery rate is as extremely low as 50% or less, so the prior art has a technical problem in that it is impossible to use for practical removal of the extractable materials.

It is known that Inbicon, a Danish company specializing in the production of bioethanol with lignocellulosic biomass as a raw material, removes not only extractable materials in biomass but also a liquid containing a large amount of microbial inhibitors by using a process which performs liquid hot water pretreatment of biomass, solid-liquid separation, and subsequent washing the pretreated solid with water (Jan Larsen et al., 2012, Biomass and Bioenergy, 46, 36-45). This method has an advantage in that a clean pretreated solid used to produce a good quality of fermentable sugar can be obtained, but a production cost inevitably increases due to solid-liquid separation and repeated washing. Also, there is a need to perform a process in which a predetermined amount of pretreated liquids containing microbial growth inhibitors should be additionally fed in order to prevent the contamination by lactic acid bacteria during enzymatic hydrolysis or alcohol fermentation, and as a consequence, there is no choice but to add extractable materials of biomass of which composition cannot be known due to a more complex composition caused by a high temperature and pressure reaction. In addition, because a liquid obtained, as a by-product, after pretreatment of biomass contains not only xylose and xylan but also overdegradation products of carbohydrate such as furfural and 5-hydroxymethyl-2-furfural (hereinafter referred to as 'HMF'), chemically altered proteins produced by the maillard reaction at high temperature of, for example, 190° C., a variety of organic acids, lignin degradation products and a variety of inorganic salts, it is difficult for this by-product to make high value added products but relatively low value added fertilizers.

In producing glucose from lignocellulosic biomass, because only the use of biomass in ground form is not sufficient for converting cellulose to glucose, it is general to perform pretreatment and saccharification processes in a sequential order. The pretreatment of biomass refers to a process which treats ground or crushed biomass by a physicochemical method to bring each structural component of biomass into an easy state to fractionation. During pretreatment of biomass, hemicellulose or lignin surrounding cellulose is degraded or dissolved and released in part or in whole, so that the cellulose becomes more susceptible to be hydrolyzed. The saccharification of biomass refers to conversion of cellulose to glucose by a physicochemical or biochemical method after pretreatment described as the above.

Provided that means for cellulose hydrolysis is limited to enzymes in the saccharification process, the technique being widely used for pretreatment of biomass includes liquid hot water pretreatment (autohydrolysis or hydrothermolysis), dilute acid pretreatment, lime pretreatment, ammonia pretreatment (ARP, etc.), and steam explosion. These pretreatment techniques make cellulose susceptible to hydrolytic enzymes better through a pretreatment by which hemicellulose or lignin in biomass is primarily removed. But, based on the type of biomass and reaction condition, not only the pretreatment efficiency greatly changes, but also the type and amount of materials newly produced other than sugar in the pretreatment or saccharification greatly changes as well. Recently, among these techniques, more attention is paid to liquid hot water pretreatment technique, because it is a simple and most economical process while at the same time having high applicability to a variety of biomasses.

The enzymatic hydrolysis of the pretreatment product refers to a process which converts cellulose to glucose by adding a cellulase formulation to the pretreatment product containing cellulose that is already made more susceptible to enzymes. In this instance, to promote the hydrolysis reaction, the cellulase additionally contains a variety of enzymes such as hemicellulases, starch hydrolase and pectinase in consideration of the pretreatment technique previously applied.

The sugar containing product produced through pretreatment and saccharification of lignocellulosic biomass as a raw material may be used largely for two purposes. First, there is a simultaneous saccharification and co-fermentation method. In this method, fermentation strains and additives are added either directly to a saccharification product in which monosaccharide mainly including glucose is dissolved, but solid residues after hydrolysis (hereinafter referred to as 'hydrolysis residue') are also contained (hereinafter referred to as 'saccharification product'), or to a pretreatment product containing a slight amount of glucose produced by initiation of enzymatic saccharification. Currently, this method is being widely used in research and practical production of bioalcohol. The other methods is that primarily a sugar solution is obtained through solid-liquid separation after saccharification is completed and then uses it as fermentable sugar.

The sugar solution prepared by physicochemical pretreatment and enzymatic hydrolysis of lignocellulosic biomass contains not only monosaccharide including glucose but also many materials as impurities. A typical impurity includes aldehydes produced by overdegradation of sugar such as furfural and HMF, organic acids such as levulinic acid and formic acid, and alcohols such as methanol, and besides, may include acetic acids produced by hydrolysis of hemicellulose and many phenolic compounds produced by degradation of lignin. These impurities may act as microbial growth inhibitors or metabolite production inhibitors depending on the type of fermentation strains. Reportedly, phenolic compounds that are lignin degradation products contained in a sugar solution are commonly the strongest microbial inhibitor, furfural and HMF may serve as a selective inhibitor depending on the concentration, and a variety of acids such as acetic acid may vary in physiological reaction for each strain. When cultivating *Clostridium beijerinckii* using a sugar solution prepared from corn stover by dilute acid pretreatment using sulfuric acid and enzymatic hydrolysis, furfural and HMF promoted the growth of the strains, while phenolic compounds such as syringaldehyde inhibited the their growth (Thaddeus Ezeji et al, *Biotechnology and Bioengineering*, 97(6), 1460-1468, 2007). In the study, in which each material was added to an artificially prepared sugar solution at each concentration, and growth was tested using yeast as an ethanologen, furfural did not affect the ethanol production, while HMF had a slight influence, and acetic acid inhibited the growth markedly with the increasing concentration (Jeffrey D. Keating et al, 2006, *Biotechnology and Bioengineering*, 93(6), 1196-1206). Also, it was reported that phenolic compounds greatly inhibited the growth of yeast, and inhibition performance in the case where acetic acid and furfural were used together was greater than the case where acetic acid and furfural were used singly. In the case of *Corynebacterium glutamicum* as an ethanologen, the growth was inhibited with the increasing concentration of furfural and HMF, and this growth inhibition was more sensitive to *Zymomonas mobilis* and *E. coli* (Shinsuke Sakai et al, *Applied and Environmental Microbiology*, 2349-2353, 2007). Also, phenolic compounds such as syringaldehyde severely inhibited the growth of the strains, but reportedly, the influence of acetic acid was not great. Such microbial inhibitors contained in a sugar solution produced from lignocellulosic biomass may have different influences on the growth and metabolite production according to the type of microorganisms, so it is not easy to assure a general tendency without any direct application.

Thus, to use the saccharification product produced from biomass intactly for microbial fermentation, attempts have been made to improve fermentation strains molecular biologically or select suitable microorganisms from new strains to avoid the influence by many impurities or efficiently produce metabolite. From a long time ago, an ethanologen or yeast used for humans to produce many types of alcoholic beverages is said to one of fermentation strains having highest resistance to microbial inhibitors, and recently, the intensive studies are being made to make the strains suitable for production of bioalcohol using a lignocellulosic sugar solution. Lactic acid bacteria that is ubiquitous in daily life is also known as a relatively less vulnerable strain.

In contrast, generally, most of industrial microbes including *E. coli* or *Clostridium acetobutylicum* are greatly inhibited in growth or metabolite production by several impurities. Thus, for detoxification of many microbial inhibitors contained in a sugar solution prepared from lignocellulosic biomass, many studies have been made, for example, overliming, polymerization using lignin peroxidase, etc. Many other researchers are applying various types of chromatographies using adsorption and partition to removal approach of these materials (Villarreal, M. L. M. et al, *Enzyme and Micrbial Technology*, 40, 17-24, 2006).

On the other hand, to minimize an amount of microbial inhibitors contained in a sugar solution, a method that washes a pretreatment product with excess water before enzymatic hydrolysis is being used. It is known that Inbicon, now running a pilot plant scale bioalcohol production facility, uses a method which performs liquid hot water pretreatment of biomass, removes a liquid phase of pretreatment product containing a large amount of microbial inhibitors by solid-liquid separation and then washes the pretreated solid with water (Jan Larsen et al, 2012, *Biomass and Bioenergy*, 46, 36-45). However, it is susceptible to contamination by unwanted microorganisms such as lactic acid bacteria at the initial stage of enzymatic hydrolysis or alcohol fermentation after washing the pretreatment product, therefore, to prevent this, an aliquot of the pretreatment liquid containing microbial growth inhibitors is added back. Also, during enzymatic hydrolysis and ethanol fermentation, microbial inhibitors such as acetic acid and phenolic compounds are released from the pretreatment product, so this method is very useful for alcohol fermentation using yeast having strong resistance to microbial inhibitors, but there is no report on its application to fermentable sugar production for a wide use. Also, in the case of a pretreatment product having a reduction in average diameter by grinding or pretreatment, a portion of the finely particulated pretreatment product may be lost during washing, involving a risk of sugar yield reduction.

Lignocellulosic biomass includes a small amount of extractable materials that can be extracted with water or organic solvents, and structural components that are polymerized and are not dissolved in water or organic solvents. Cellulose is one of structural components of lignocellulosic biomass, occupies 25% to 60% of biomass, and is a polymer made by dehydration condensation of glucose. When producing fermentable sugar using biomass as a raw material, cellulose in biomass is a main target for acid hydrolysis or enzymatic hydrolysis, but because cellulose is surrounded by other structural components, hemicellulose and lignin, cellulose is not easily fractionated.

One of structural components of lignocellulosic biomass, hemicellulose (15 to 35%), has glucose, galactose, mannose and arabinose as side chains linked to the xylan skeleton formed by dehydration condensation of xylose, and acids such as glucuronic acid and acetic acid bonded by ester linkages, and thus, hydrolysis is relatively easy. In contrast, because lignin (10 to 30%) is a polymer having a complex structure of lignan which is an aromatic compound, it is less susceptible to hydrolysis by acids, but is soluble in alkali.

When producing fermentable sugar by enzymatic hydrolysis of cellulose using lignocellulosic biomass as a raw material, to help the action of a cellulolytic enzyme, it is general to first perform physicochemical or biological pretreatment of biomass. The saccharification of biomass by enzymes represents adding cellulase or a mixture of cellulase and hemicellulase to the pretreatment product to hydrolyze cellulose or hemicellulose for a predetermined time to thereby convert to a sugar solution containing glucose and xylose as a primary ingredient.

Liquid hot water pretreatment (autohydrolysis or hydrothermolysis) widely used in pretreatment of herbaceous biomass is a simple technique that puts biomass and water in a high pressure reactor, followed by sealing and causing a reaction at 160° C. to 220° C. for a predetermined time. In this liquid hot water pretreatment, hemicellulose in lignocellulosic biomass is hydrolyzed first and is then released to water by xylooligosaccharides together with xylose, and generally, most of herbaceous and woody biomass shows a maximum yield at 180 to 190° C. Subsequently, the concentration of xylose and xylooligosaccharides detected in water reduces rapidly with the temperature, which is because xylose is degraded further to produce an overdecomposition product such as furfural at a much higher rate than a rate at which hemicellulose in biomass is hydrolyzed and releases xylose to water. However, the concentration of acetic acid in the pretreated liquid gradually increases from 160° C. or lower to 220° C. or higher, and it is thought that most of acetic acid is a hydrolysate of acetyl groups attached to the xylan skeleton of hemicellulose by ester linkages.

Generally, it is said that a drawback of liquid hot water pretreatment is a slightly low sugar yield after enzymatic hydrolysis when compared to dilute acid pretreatment that mainly employs a low concentration of sulfuric acid or hydrochloric acid in pretreatment. In addition, when hemicellulose remaining by imperfect hydrolysis during pretreatment is hydrolyzed by enzymes in a saccharification process, organic acids such as acetic acid are bound to be released, therefore, after enzymatic hydrolysis, such acids are contained in a sugar solution.

The fermentable sugar produced by liquid hot water pretreatment and enzymatic hydrolysis using lignocellulosic biomass as a raw material contains furfural, 5-hydroxymethyl-2-furaldehyde (HMF), phenolic substances and acetic acid as impurities, and these materials are known as inhibiting the microbial growth or metabolite production based on the type of fermentation strains. Reportedly, in the study in which each material was added to an artificially prepared sugar solution at each concentration and growth was tested using yeast as an ethanologen, furfural did not affect the ethanol production, while HMF had a slight influence, but acetic acid inhibited the growth markedly with the increasing concentration (Jeffrey D. Keating et al, 2006, *Biotechnology and Bioengineering*, 93(6), 1196-1206). Also, it was reported that phenolic compounds greatly inhibited the growth of yeast, and inhibition performance in the case where acetic acid and furfural were used together was greater than the case where acetic acid and furfural were used singly.

Generally, most of industrial microbes including *E. coli* or *Clostridium acetobutylicum* are greatly inhibited in growth or metabolite production by several impurities. Thus, for detoxification of many microbial inhibitors contained in a sugar solution prepared from lignocellulosic biomass, many studies have been made, for example, overliming, polymerization using lignin peroxidase, etc. Many other researchers are applying various types of chromatographies using adsorption and partition to removal approach of these materials (Villarreal, M. L. M. et al, *Enzyme and Micrbial Technology*, 40, 17-24, 2006).

Particularly, many attempts are being made, for example, technology using adsorption chromatography to remove acetic acid contained in a sugar solution (Hee-Geun Nam, Sungyong Mun, 2012, *Process Biochemistry*, 47, 725-734; S. Ranil Wickramasinghe, David L. Grzenia, 2008, *Desalination*, 234, 144-151), and technology using a separation membrane (David L. Grzenia et al, 2012, *Journal of Membrane Science*, 415-415, 75-84; Sung-Jae Kim et al, 2012, *Process Biochemistry*, 47, 2051-2057].

Overliming for detoxification of a sugar solution is lowest cost and is being widely used, and includes adding and dissolving lime until pH of a sugar solution reaches 10 and heating at 60° C. or less for a predetermined time. As a result, many impurities such as furfural, HMF, protein, etc. may be deposited and removed by filtration or deposition. However, a loss of hemicellulose sugar is generally accompanied during the process.

On the other hand, to minimize an amount of microbial inhibitors contained in a sugar solution, a method that washes a pretreatment product with excess water before enzymatic hydrolysis is being used. It is known that Inbicon, now running a pilot plant scale bioalcohol production facility, uses a method which performs liquid hot water pretreatment of biomass, removes a liquid phase of pretreatment product containing a large amount of microbial inhibitors by solid-liquid separation and then washes the pretreated solid with water (Jan Larsen et al, 2012, *Biomass and Bioenergy*, 46, 36-45). However, during enzymatic hydrolysis and ethanol fermentation, microbial inhibitors such as acetic acid and phenolic compounds are released from the pretreatment product, and thus, there will be a need for more research and development to apply this method to fermentable sugar production suitable for cultivation of other fermentation strains.

Another method for removing acetic acid from biomass is a method that adds sodium hydroxide to biomass, hydrolyzes acetiyl group in hemicellulose by heating, elutes acetic acid, and carries out solid-liquid separation, and washes out with water to remove acetic acid (Cho, D. H. et al, 2010, *Bioresource Technology*, 10, 4947-4951). In the case that this method is performed before dilute acid pretreatment of biomass, this method is available because acids are added as a catalyst for pretreatment. That is, biomass having undergone hydrolysis and removal of acetic acid contained in hemicellulose by strong alkali treatment beforehand cannot be expected to undergo a hydrolysis reaction of the hemicellulose main chain by the action of the acid catalyst, so unless acids are artificially added, it should be heated at 230° C. to 250° C. or higher to expect a pretreatment effect. This pretreatment technique is known as pH-controlled liquid hot water pretreatment.

Cellulose that is a structural component of lignocellulosic biomass and a direct raw material for fermentable sugar production occupies 25% to 60% of biomass, and is a polymer made by dehydration condensation of glucose. When producing glucose by acid hydrolysis or enzymatic hydrolysis of cellulose, hemicellulose and lignin included in lignocellulosic biomass acts as a barrier. Thus, before cellulose hydrolysis, pretreatment of biomass for chemically degrading either hemicellulose or lignin or breaking of its rigid structure is essential.

Because hemicellulose (15 to 35%) making up lignocellulosic biomass includes glucose, galactose, mannose and arabinose as side chains linked to the xylan skeleton formed by dehydration condensation of xylose, and organic acids such as uronic acid and acetic acid bonded by ester linkages, hydrolysis by acid catalysts is relatively easy.

Liquid hot water pretreatment (autohydrolysis or hydrothermolysis) or dilute acid treatment widely used for pretreatment of herbaceous biomass to produce fermentable sugar by hydrolyzing biomass using enzymes is technique that puts biomass and water or acids in a high pressure reactor, followed by sealing and causing a reaction at 140° C. to 230° C. for a predetermined time. Hemicellulose in lignocellulosic biomass is hydrolyzed by acid-catalytic pretreatment and released to water by xylooligosaccharides together with xylose, and in this instance, acetyl groups attached to the xylan main chain in hemicellulose by ester linkages are hydrolyzed and released together.

However, the ratio of acetic acid hydrolyzed and released from hemicellulose changes depending on the severity of the pretreatment process, and acetyl groups remaining in unreacted state are hydrolyzed and released in the subsequent enzymatic hydrolysis or acid hydrolysis. To hydrolyze and remove all acetyl groups in hemicellulose during acid catalyst pretreatment, the acid concentration or pretreatment temperature should be increased. However, it is known that at such a high severity, xylose produced by hydrolysis of hemicellulose is overdegraded, yielding 2-furfural, acetic acid and formic acid, and glucose is overdegraded, yielding 5-hydroxymethyl-2-furaldehyde (HMF) and levulinic acid.

In contrast, if the severity of pretreatment is reduced to avoid overdegradation of carbohydrate, when hemicellulose remaining by incomplete hydrolysis in the pretreatment process is hydrolyzed by enzymes during subsequent saccharification, organic acids such as acetic acid are released. Therefore, after enzymatic hydrolysis, such acids are contained in a sugar solution.

The fermentable sugar produced by liquid hot water pretreatment and enzymatic hydrolysis using lignocellulosic biomass as a raw material contains furfural, 5-hydroxymethyl-2-furaldehyde (HMF), phenolic substances and acetic acid as impurities, and these materials are known as inhibiting the microbial growth or metabolite production based on the type of fermentation strains. Reportedly, in the study in which each material was added to an artificially prepared sugar solution at each concentration and growth was tested using yeast as an ethanologen, furfural did not affect the ethanol production, while HMF had a slight influence, but acetic acid inhibited the growth markedly with the increasing concentration (Jeffrey D. Keating et al, 2006, *Biotechnology and Bioengineering*, 93(6), 1196-1206). Also, it was reported that phenolic compounds greatly inhibited the growth of yeast, and inhibition performance in the case where acetic acid and furfural were used together was greater than the case where acetic acid and furfural were used singly.

Generally, most of industrial microbes including *E. coli* or *Clostridium acetobutylicum* are greatly inhibited in growth or metabolite production by several impurities. Thus, for detoxification of many microbial inhibitors contained in a sugar solution prepared from lignocellulosic biomass, many studies have been made, for example, overliming, polymerization using lignin peroxidase, etc. Many other researchers are applying various types of chromatographies using adsorption and partition to removal approach of these materials (Villarreal, M. L. M. et al, *Enzyme and Micrbial Technology*, 40, 17-24, 2006).

Particularly, many attempts are being made, for example, technology using adsorption chromatography to remove acetic acid contained in a sugar solution (Hee-Geun Nam, Sungyong Mun, 2012, *Process Biochemistry*, 47, 725-734; S. Ranil Wickramasinghe, David L. Grzenia, 2008, *Desalination*, 234, 144-151), and technology using a separation membrane (David L. Grzenia et al, 2012, *Journal of Membrane Science*, 415-415, 75-84; Sung-Jae Kim et al, 2012, *Process Biochemistry*, 47, 2051-2057].

Overliming for detoxification of a sugar solution is lowest cost and is being widely used, and includes adding and dissolving lime until pH of a sugar solution reaches 10 and heating at 60° C. or less for a predetermined time. As a result, many impurities such as furfural, HMF, protein, etc. may be deposited and removed by filtration or deposition. However, a loss of hemicellulose sugar is generally accompanied during the process.

Another method for removing acetic acid from biomass is a method that adds sodium hydroxide to biomass, hydrolyzes acetiyl group in hemicellulose by heating, elutes acetic acid, and carries out solid-liquid separation, and washes out with water to remove acetic acid (Cho, D. H. et al, 2010, *Bioresource Technology*, 10, 4947-4951). In the case that this method is performed before dilute acid pretreatment of biomass, this method is available because acids are added as a catalyst for pretreatment. That is, biomass having undergone hydrolysis and removal of acetic acid contained in hemicellulose by strong alkali treatment beforehand cannot be expected to undergo a hydrolysis reaction of the hemicellulose main chain by the action of the acid catalyst, so unless acids are artificially added, it should be heated at 230° C. to 250° C. or higher to expect a pretreatment effect. This pretreatment technique is known as pH-controlled liquid hot water pretreatment.

On the other hand, to minimize an amount of microbial inhibitors contained in a sugar solution, a method that washes a pretreatment product with excess water before enzymatic hydrolysis is being used. It is known that Inbicon, now running a pilot plant scale bioalcohol production facility, uses a method which performs liquid hot water pretreatment of biomass, removes a liquid phase of pretreatment product containing a large amount of microbial inhibitors by solid-liquid separation and then washes the pretreated solid with water (Jan Larsen et al, 2012, *Biomass and Bioenergy*, 46, 36-45). However, during enzymatic hydrolysis and ethanol fermentation, microbial inhibitors such as acetic acid and phenolic compounds are released from the pretreatment product, and thus, there will be a need for more research and development to apply this method to fermentable sugar production suitable for cultivation of other fermentation strains.

Recently, as a new technique for minimizing an amount of acetic acid produced in the stage of enzymatic hydrolysis, washing a pretreatment product with an aqueous alkaline solution prior to the enzymatic hydrolysis has been suggested (Korean Patent Application No. 10-2013-0082290). But alkali chemicals and excess water are needed, and at least two processes are added, so the cost increase is inevitable in fermentable sugar production.

Lignocellulosic biomass primarily including aboveground plants consists of three kinds of polymers, i.e., cellulose, hemicellulose, and lignin, as structural components forming the structures of the plants, and has many additional materials that can be extracted with water or solvents. Starch that is a storage form of glucose in plants is included in the 'total glucan' with cellulose. Glucose made from the total glucan is used as a main carbon source for microorganisms in fermentative production of bioalcohol such as bioethanol or biobuthanol, monomers for biopolymer synthesis such as lactic acid and succinic acid, and metabolite such as acetone and insulin.

Cellulose, one of the structural components of biomass, is not easily converted to glucose by simple acid hydrolysis or enzymatic hydrolysis, because it is densely linked with hemicellulose mainly containing pentoses such as xylose and lignin that is a polymer of phenolic compounds by many chemical bonds, so it is general to additionally hydrolyze with acids or enzymes after pretreatment that usually dissolves either hemicellulose or lignin to expose cellulose.

However, in lignocellulosic biomass containing starch, because relatively and thermochemically stable starch surrounds cellulose together with hemicellulose and lignin, the fractionation of cellulose is more difficult. When converting lignocellulosic biomass containing starch to glucose using ordinary pretreatment and saccharification techniques, pretreatment needs to be performed at higher temperature than lignocellulosic biomass containing no starch to increase the glucose yield. However, at such high temperature, a portion of starch is overdegraded, yielding 5-hydroxy-2-furaldehyde (HMF) which is a microbial growth inhibitor. And starch is first converted to glucose by enzymes during enzymatic hydrolysis, afterward the resulting glucose tends to reduce enzyme activity by feedback inhibition, which makes it difficult to increase the sugar yield.

To overcome this phenomenon, technique that first separates sap from palm trunks containing a large amount of sugar, and converts it to ethanol or lactic acid through fermentation (CN-101589151; JP-2008-178355; Akihiko Kosugi et al, 2010, Ethanol and lactic acid production using sap squeezed from old oil palm trunks felled for replanting, *Journal of Bioscience and Bioengineering*, 110(3), 322325), and technique that separates parenchyma and vascular bundles from palm trunks and, then, converts them to ethanol (Prawitwong et al, 2012, Efficient ethanol production from separated parenchyma and vascular bundle of oil palm trunk, *Bioresour. Technol.*, 125, 37-42) have ever been reported. Also, a paper investigating ethanol production in which a sugar solution is prepared from ground palm trunks by concentrated sulfuric acid pretreatment, concentrated acid hydrolysis and solid-liquid separation, followed by fermentation by yeast (Chin et al, 2010, Optimization study of ethanolic fermentation from oil palm trunk, rubberwood, and mixed hardwood hydrolysates using *Saccharomyces cerevisiae*, *Bioresour. Technol.*, 101, 3287-3291), and a paper describing that palm trunks are pretreated with aqueous ammonia, and after solid-liquid separation of the pretreatment product, and only a solid is subjected to enzymatic hydrolysis to obtain a sugar solution, followed by ethanol fermentation of the sugar solution (Jung et al, 2011, Ethanol production from oil palm trunks treated aqueous ammonia and cellulase, *Bioresour. Technol.*, 102, 7307-7312) have ever been reported.

However, to produce a fermentation product such as ethanol or lactic acid as described above, procedural manipulation at many steps is required to efficiently separate and extract starch or sugar from biomass first, so a rise in production cost is inevitable, and in spite of procedural manipulation at many steps, the ethanol yield is not high.

In keeping up with global energy security issues, for example, the climate change issue caused by exhaustion and excessive consumption of fossil fuels and $CO_2$ emission regulation, many countries in the world are dedicated towards developing alternative energy. Thus, attention is being paid to ethanol production using plant biomass such as plant wastes and woody chips with an attempt to develop alternative energy.

Plant biomass mainly includes hemicellulose, cellulose, and lignin. Cellulose is a simple polysaccharide made by dehydration condensation of glucose, and hemicellulose is a complicated polysaccharide made by dehydration condensation of glucose, xylose, mannose, etc. Thus, cellulose and hemicellulose can be converted to sugar by pretreatment technique, for example, hydrolysis, and the sugar can be used as a carbon source to produce biofuel or chemicals fermentatively.

Hydrolysis for converting cellulose or hemicellulose to fermentable sugar includes an enzymatic hydrolysis method using fungus- or bacteria-produced cellulase and a chemical saccharification method using catalysts such as acid and alkali. A typical hydrolysis method includes a concentrated sulfuric acid method, a dilute sulfuric acid method and an enzyme method. The concentrated sulfuric acid method uses higher than 70% of sulfuric acid, and cellulose and hemicellulose is hydrolyzed under the condition of around 70° C. at normal pressure. After hydrolysis, the produced monosaccharide and sulfuric acid are separated, and sulfuric acid is recycled. The concentrated sulfuric acid method is characterized by a high sugar recovery and applicability to various raw materials. The dilute sulfuric acid method is a method that performs hydrolysis using sulfuric acid in concentration of a few % under the condition of temperature of 150~250° C. and pressure of 1~2 MPa. In this instance, because dilute sulfuric acid is used, it is general to perform neutralization treatment without recycling sulfuric acid. Because the dilute sulfuric acid method does not recover or reuse sulfuric acid, the process configuration is simple, but due to the high temperature and high pressure condition, sugar is susceptible to overdegradation, therefore, a drawback is that a recovery rate of monosaccharides is not high. The enzyme method is a method that performs hydrolysis using enzymes. Because this method should bring enzymes into contact with cellulose or hemicellulose efficiently, biomass needs to be degraded to some extent beforehand using dilute sulfuric acid or vapor. Also, there is a need for development to prepare a special enzyme for efficiently breaking the strong linkages between each structural components using genetic modification technology. A primary facility of the enzyme method only involves mixing of enzymes and biomass in a tank, so a low facility cost is an advantage, but a high production cost of enzymes is a disadvantage.

In hydrolysis of cellulose-containing biomass, cellulose or hemicellulose are degraded, while at the same time, producing by-products, for example, furan compounds such as furfural, hydroxymethylfurfural, etc., or organic acids such as formic acid, acetic acid, levulinic acid, etc. Also, because cellulose-containing biomass contains lignin that are aromatic polymers, during acid pretreatment, lignin substances are degraded, and by-products, for example, aromatic compounds such as low molecular weight phenolic compounds are produced. These compounds inhibitively acts on a fermentation process using microorganisms to cause microbial growth inhibition, and reduce the yield of fermentation products, so they are called fermentation inhibitors, and need to be removed when a biomass derived sugar solution is used as a fermentation raw material.

As a conventional method of removing fermentation inhibitors in a preparation process of a sugar solution, Korean Patent Publication No. 2011-94005 discloses a method for preparing a sugar solution, including a process of hydrolyzing cellulose-containing biomass to prepare an aqueous sugar solution; and a process of filtering the obtained aqueous sugar solution through a nanofiltration membrane and/or reverse osmosis membrane to recover a refined sugar solution from the non-permeate side and remove fermentation inhibitors from the permeate side. However, the method is easy to separate fermentation inhibitors but is undesirable in that monosaccharides such as glucose, xylose, etc., are released together.

In this context, the inventors discovered that when a polyamide nanofiltration membrane is modified to reduce surface charge, and an aqueous sugar solution is filtered using the modified polyamide nanofiltration membrane, fermentation inhibitors can be removed and a refined sugar solution is able to be prepared, and thereby, completed the invention.

DISCLOSURE

Accordingly, the present disclosure is directed to providing a method for producing bioethanol from lignocellulosic biomass at high yields by minimizing microbial inhibitors using a series of pretreatment and enzymatic hydrolysis processes for preventing the occurrence of growth inhibitors to industrial fermentation strains to the maximum while maximizing the sugar yield.

Also, the present disclosure is directed to providing washing technique of a biomass pretreatment product to remove chemicals that inhibit the growth of industrial fermentation strains, in particular, acetic acid from a biomass pretreatment product while maximizing the sugar yield by subsequent enzymatic hydrolysis.

Also, the present disclosure is directed to providing enzymatic hydrolysis technique for reducing toxicity of growth inhibitors of industrial fermentation strains, in particular, acetic acid produced from a biomass pretreatment product.

Also, the present disclosure is directed to providing a method for producing microbial metabolite such as bioethanol or lactic acid at high yields from lignocellulosic biomass containing starch.

Also, the present disclosure is directed to providing a method for preparing a high concentration and high purity of sugar solution by removing fermentation inhibitors and concentrating a sugar solution using a separation membrane.

To achieve the above object, the present disclosure provides a method for producing bioethanol from lignocellulosic biomass, the method including the steps of:

1) adding water to coarsely ground or powdery lignocellulosic biomass and heating at 50 to 140° C. for 1 to 60 minutes, followed by dehydration (removal step for hot water extractives);

2) adding water to a solid obtained at the step 1 and performing liquid hot water pretreatment at 170 to 210° C. for 1 minute to 30 minutes (liquid hot water pretreatment step);

3) obtaining a solid including a small amount of liquid from the liquid hot water pretreatment product obtained at the step 2 by solid-liquid separation (solid-liquid separation step);

4) performing enzymatic hydrolysis of the solid obtained at the step 3 by a cellulase enzyme complex at 45 to 55° C. (enzymatic hydrolysis step);

5) recovering a sugar solution from the saccharification product obtained at the step 4 through repeated processes of solid-liquid separation and extraction (sugar solution recovery step);

6) performing filtration, concentration and impurity removal of the sugar solution obtained at the step 5 to obtain fermentable sugar (fermentable sugar obtaining step); and 7) fermenting the fermentable sugar obtained at the step 6 using an ethanologen (alcohol fermentation step).

The method of the present disclosure removes a majority of extractable materials such as protein and inorganic salts by extracting biomass with hot water before pretreatment, thereby minimizing the content of impurities in substrate for enzymatic hydrolysis, and pretreats biomass from which hot water extractable materials are removed under the condition in which the hemicellulose sugar yield is at maximum, to produce fermentable sugar for alcohol fermentation only by concentration using a separation membrane without washing the pretreated solid obtained by subsequent solid-liquid separation with water. Also, a load amount of impurities is reduced during subsequent additional refining, so a refining cost is curtailed, and there is no loss of cellulose caused by washing the pretreatment product before enzymatic hydrolysis, so a high sugar yield is maintained, while at the same time, producing bioethanol without unwanted microbial contamination such as lactic acid bacteria during the enzymatic hydrolysis period by a minimum of microorganism growth inhibitors present in the pretreatment product and enzymatic hydrolysis performed at high temperature. Further, biomass usage efficiency may be maximized by respectively recovering hot water extractable materials contained in raw materials biomass and relatively pure pretreated liquid containing xylooligosaccharides which may become a raw material of dietary fiber or xylitol, and by using them as raw materials.

To achieve the above object, the present disclosure provides a method for producing fermentable sugar from lignocellulosic biomass in which acetic acid was removed, the method including the steps of:

1) adding water to coarsely ground or powdery lignocellulosic biomass and performing liquid hot water pretreatment, and performing solid-liquid separation of the obtained pretreatment product to obtain a solid;

2) adding an aqueous alkali solution warmed at room temperature to 100° C. or less to the solid obtained at the step 1), mixing them and dehydrating to recover the solid; and 3) adding a cellulose hydrolysis enzyme to the solid obtained at the step 2) to perform enzymatic hydrolysis.

After liquid hot water pretreatment of biomass, the method of the present disclosure removes an acetyl group remaining in the pretreated solid in unreacted state before enzymatic hydrolysis, thereby significantly reducing the concentration of acetic acid contained in a sugar solution obtained by enzymatic hydrolysis, and as a result, preparing fermentable sugar that can cultivate many industrial fermentation strains, and particularly, even microorganism of which growth may be inhibited by acetic acid. Also, a pretreatment effect is enhanced during an acetyl group removal process, thereby not only greatly increasing the sugar yield achievable by enzymatic hydrolysis but also significantly reducing the content of impurities in the sugar solution by the washing effect of the pretreatment product.

To achieve the above object, the present disclosure provides a production method of fermentable sugar having reduced toxicity of acetic acid, the method including the steps of:

1) performing liquid hot water pretreatment of lignocellulosic biomass to produce a pretreatment product for enzymatic hydrolysis; and 2) adding a cellulose hydrolysis enzyme to the pretreatment product obtained at the step 1, and adding an alkali reagent including a base with at least two hydroxyl groups in its molecule, having a dissolution constant ($pKa_2$) of 8.0 or more for a second acetyl group of acetate, to perform enzymatic hydrolysis.

Also, the present disclosure provides a method for fermentation of microorganisms using fermentable sugar having reduced toxicity of acetic acid produced by the above method.

When acetic acid included in the pretreatment product and an acetyl group remaining in unreacted state in the pretreatment solid after liquid hot water pretreatment of biomass is hydrolyzed in enzymatic hydrolysis and eluted in water, the method of the present disclosure performs neutralization using an alkali reagent including a base with at least two hydroxyl groups, having a dissolution constant ($pKa_2$) of 8.0 or more for a second acetyl group of acetate, so it can be expected an effect of reducing the biological concentration of acetic acid which inhibits the microbial growth in the subsequent microbial fermentation less than ½.

In one embodiment of the present disclosure according to the object, there is provided a method for producing microbial metabolite from lignocellulosic biomass containing starch, the method including the steps of: 1) performing liquid hot water pretreatment of ground lignocellulosic biomass containing starch using steam or water under the following condition: a) a temperature range of 170° C. to 230° C. and b) a reaction time at which the yield of hemicellulose sugar produced at the step 2) is at maximum; 2) saccharifying the entire pretreatment product using cellulase or cellulase enzyme complex without solid-liquid separation; and 3) adding microorganisms to the saccharification product to perform fermentation.

In another embodiment of the present disclosure according to the object, there is provided a method for producing microbial metabolite from lignocellulosic biomass containing starch, the method including the steps of: 1) gelatinizing and swelling ground lignocellulosic biomass containing starch using boiling water or steam; 2) adding starch hydrolase to the gelatinized and swollen biomass meal to hydrolyze the starch; 3) adding microorganisms to the hydrolyzed biomass meal to perform fermentation; 4) performing liquid hot water pretreatment of the fermented biomass meal using steam or water under the following condition: a) a temperature range of 170° C. to 230° C. and b) a reaction time at which the yield of hemicellulose sugar produced at the step 5) is at maximum; 5) saccharifying the entire pretreatment product using cellulase or cellulase enzyme complex without solid-liquid separation; and 6) adding microorganisms to the saccharification product to perform fermentation.

The method of the present disclosure performs liquid hot water pretreatment of lignocellulosic biomass containing starch under the condition in which the yield of hemicellulose sugar is at maximum, thereby suppressing the production of carbohydrate overdegradation products at the minimum, and uses the entire pretreatment product of biomass without solid-liquid separation, thereby preventing a loss of starch or sugar and maximizing the usage efficiency of cellulose and hemicellulose. Also, the method of the present disclosure minimizes feedback inhibition of cellulase by glucose by conversion of glucose to metabolite by microorganisms, making maximum use of starch and cellulose contained in biomass, thereby producing microbial metabolite at high yields by a simple process.

To solve the problem, the present disclosure provides a method for preparing a sugar solution, the method including the following steps of:

1) modifying a polyamide nanofiltration membrane with sodium hypochlorite and polyethylene glycol methacrylate (step 1); and 2) filtering an aqueous sugar solution obtained by hydrolyzing cellulosic biomass using the modified polyamide nanofiltration membrane to recover a refined sugar solution from the non-permeate side and remove fermentation inhibitors from the permeate side (step 2).

Preferably, the method may further include the step of, between the step 1) and the step 2), filtering the aqueous sugar solution obtained by hydrolyzing the cellulosic biomass using a microfiltration membrane or ultrafiltration membrane to recover a sugar solution from the permeate side (step 1-1).

Preferably, the method may further include the step of, after the step 2), filtering the refined sugar solution using a reverse osmosis membrane to recover a refined sugar solution from the non-permeate side and remove fermentation inhibitors from the permeate side (step 2-1).

The method for preparing a sugar solution using a separation membrane according to the present disclosure modifies a polyamide nanofiltration membrane to reduce surface charge and filters an aqueous sugar solution using the modified polyamide nanofiltration membrane, thereby removing fermentation inhibitors and preparing a refined sugar solution, and particularly, increases the removal percent of fermentation inhibitors by using a constant volume filtration method, thereby providing a preparation effect of a high concentration and high purity sugar solution.

BRIEF DESCRIPTION OF DRAWINGS

FIG. 1 is a graph showing the measured yields of hemicellulose sugars obtained by enzymatic hydrolysis based on reaction temperature and reaction time in liquid hot water pretreatment of palm trunks.

DETAILED DESCRIPTION

A Method for Producing Bioethanol from Lignocellulosic Biomass

The present disclosure provides a method for producing bioethanol from lignocellulosic biomass, including the steps of:

1) adding water to coarsely ground or powdery lignocellulosic biomass and heating at 50 to 140° C. for 1 to 60 minutes, followed by dehydration (removal step for hot water extractable material);

2) adding water to a solid obtained at the step 1 and performing liquid hot water pretreatment at 170 to 210° C. for 1 minute to 30 minutes (liquid hot water pretreatment step);

3) obtaining a solid including a small amount of liquid from the liquid hot water pretreatment product obtained at the step 2 by solid-liquid separation (solid-liquid separation step);

4) performing enzymatic hydrolysis of the solid obtained at the step 3 by a cellulase enzyme complex at 45 to 55° C. (enzymatic hydrolysis step);

5) recovering a sugar solution from the saccharification product obtained at the step 4 through repeated processes of solid-liquid separation and extraction (sugar solution recovery step);

6) performing filtration, concentration and impurity removal of the sugar solution obtained at the step 5 to obtain fermentable sugar (fermentable sugar obtaining step); and 7) fermenting the fermentable sugar obtained at the step 6 using an ethanologen (alcohol fermentation step).

The term 'fermentable sugar' as used herein represents a sugar substance used for alcohol fermentation to produce bioethanol or the like, and can be interchangeably used with sugar for fermentation or fermentable sugar.

The technical subject matter of the bioethanol production method of the present disclosure is characterized by producing bioethanol at high yields with a minimum content of impurities such as microbial inhibitors through a series of processes including a removal step for hot water extractable materials from biomass, a liquid hot water pretreatment step, a solid-liquid separation step, an enzymatic hydrolysis step, a sugar solution recovery step, a fermentable sugar obtaining step and an alcohol fermentation step.

In the method of the present disclosure, the first process, i.e., the removal step for hot water extractable materials is a step of adding water to coarsely ground or powdery lignocellulosic biomass and heating at 50 to 140° C. for 1 to 60 minutes, followed by dehydration. The process is effective in increasing the saccharification rate and sugar yield by minimizing an amount of materials which inhibit the activity of cellulose hydrolysis enzymes such as inorganic salts in large amounts within herbaceous biomass during subsequent enzymatic hydrolysis of the pretreatment product, and curtailing a process cost by reducing a load amount of impurities in a refinery process of the sugar solution after enzymatic hydrolysis. Also, this process recovers useful materials, for example, starch and free sugar contained as extractable materials in biomass, proteins, lipids, pectins, tannins, alkaloids showing a variety of biological activities, organic acids and inorganic salts and uses them as resources, while at the same time, reducing the likelihood that these materials becomes useless by reactions such as degradation, condensation, and modification during pretreatment, or that protein turns into a toxic material by a maillard reaction.

The process may recover or remove extractable materials through extraction with water under the temperature at which the water solubility of materials is usually at maximum after soaking biomass in water. Preferably, after soaking biomass in water, stirring is performed at the temperature of 80 to 105° C. for 1 to 60 minutes, and an aqueous solution may be removed through solid-liquid separation before it is cooled down at the point in time when elution of extractable materials is at maximum. During this process, most of the extractable materials contained in biomass can be removed, and various extraction methods may be used in this process, for example, counter-current extraction, co-current extraction, semi-batch type extraction and batch type extraction.

The object of this process is to extract and remove a maximum of extractable materials from biomass with a minimum of hot water. The batch type extraction is performed by putting biomass meal in an extractor, performing extraction with an addition of hot water, and removing a liquid through solid-liquid separation, and in this instance, the extractable material removal efficiency increases with the increasing solid liquid ratio (a ratio of water to biomass) ranging from approximately 1:4 in weight. For example, when 1 kg biomass is put in 20 L water and heated at 95° C., and then solid-liquid separation is performed to obtain 3 kg solid and 18 L aqueous solution, 90% of extractable materials is removed and the remaining 10% is only entered into a subsequent pretreatment process. However, in terms of biomass fractionation, when the extracted product is to be used, preferably the solid liquid ratio does not exceed 1:20 in consideration of a dehydration cost and a waste water treatment cost.

The removal efficiency of extractable materials by hot water extraction of biomass increases with the increasing temperature at extraction and the increasing temperature at solid-liquid separation. This is because a majority of materials increases in water solubility with the temperature. Accordingly, extraction and solid-liquid separation is preferably performed at high temperature, for example, 50 to 140° C., preferably, 80 to 105° C. Also, as the biomass is finer, the soaking time is shorter, but when considering an energy cost for grinding and efficiency of extraction, it is advantageous to crush or comminuate first with a size that can be used in raw materials for pretreatment of biomass, for example, an average diameter of 0.1 mm to 50 mm.

The water content in solid fraction after extraction of the extractives from biomass depends on the method used and equipment applied, but approximately 50% to 90% is desirable. If necessary, continuous centrifugal separator, filter press, drum filter or screw press may be used to obtain a solid dehydrated to the maximum by the solid-liquid separation after the extraction process.

In the method of the present disclosure, the second process, i.e., the liquid hot water pretreatment step of biomass is not only for minimizing the production of microbial inhibitors but also for maximizing the sugar yield, and is liquid hot water pretreatment performed by adding water under the condition in which the yield of hemicellulose sugar including xylose and xylan is at maximum when enzymatic hydrolysis of the entire pretreatment product obtained by liquid hot water pretreatment is performed. The process may be accomplished by adding water to the solid obtained at the step 1 and performing pretreatment at 170 to 210° C. for 1 minute to 30 minutes. The liquid hot water pretreatment may be carried out by batch-type or continuous pretreatment. An amount of water added to the raw materials in liquid hot water pretreatment, that is, a solid liquid ratio is not particularly limited if it is higher than or equal to a suitable amount to cause a hydrolysis reaction of biomass, but because the present disclosure does not separately wash a reactant after pretreatment, a ratio of raw materials to water is preferably from 1:3 to 1:15 in weight ratio when considering pretreatment efficiency and carryover of microbial growth inhibitors produced during pretreatment to a subsequent process. For example, in the case of batch-type liquid hot water pretreatment of herbaceous biomass to produce fermentable sugar applicable to the multipurpose, a solid ratio to water may be set to 8% by adding water, or water and clay mineral to the solid recovered from sunflower stalks powder through the above mentioned step 1, and it is put in a high pressure reactor to conduct a reaction at 190° C. for 5 minutes (see Korea Patent Publication No. 2012-73087 and WO/2012/087068). At this temperature, the yield of xylose and xylan produced by hydrolysis of hemicellulose is at maximum, while an amount of furfural that tends to be decomposed further and HMF produced by decomposition of cellulose is at minimum. On the other hand, the yield of glucose that may be produced in enzymatic hydrolysis after pretreatment is lower than that of pretreatment performed under severer conditions, and to increase the sugar yield, techniques using clay minerals in enzymatic hydrolysis (Korea Patent Publication No. 2012-73087 and WO/2012/087068) or polyethyleneglycol (U.S. Pat. No. 7,972,826) may be used.

In the method of the present disclosure, the third process, i.e., the solid-liquid separation step is a step of obtaining a solid including a small amount of liquid from liquid hot water pretreatment product obtained at the step 2 by solid-liquid separation. The solid-liquid separation process may be performed by all solid-liquid separation processes commonly used in the art, and its example includes centrifugal separation, suction filtration and pressure filtration. The pretreated solid obtained by solid-liquid separation may contain a pretreated liquid about 2 to 4 times of its weight as much, and the bioethanol production method of the present disclosure feeds the pretreated solid in a subsequent saccharification process by cellulase enzyme complex without washing with hot water like many research papers. The pretreated liquid contained in the solid after solid-liquid separation is preferably adjusted to contain 5% to 30% of liquid included in the pretreatment product immediately after pretreatment. The liquid contains a suitable amount of microbial growth inhibitors for inhibiting the microbes that may often be contaminated from the air, such as lactic acid bacteria, at the optimum temperature for cellulose hydrolysis enzymes, around 50° C., so it can make enzymatic hydrolysis of the pretreatment product perform for 72 hours or longer without separate sterilization treatment. Also, the liquid may help inhibit contamination by microorganisms during the subsequent process for enzyme recovery or removal after enzymatic hydrolysis, and the concentration process using a membrane separation, by maintaining the temperature of the sugar solution above 50° C.

The pretreated liquid recovered by solid-liquid separation contains a small amount of xylose, a large amount of xylooligosaccharides, acetic acid, a trace of furfural produced by hydrolysis of hemicellulose, and water-soluble lignin degradation product. And, because most of the impurities are removed by the above mentioned step 1 of the present disclosure, the pretreated liquid recovered may be used as a raw material good for re-processing it to xylitol or dietary fiber.

In the method of the present disclosure, the fourth step, i.e., the enzymatic hydrolysis step is enzymatic hydrolysis of the solid obtained at the step 3 at pH of 4.8 to 5.2 at 45 to 55° C. The process is for converting cellulose and hemicellulose contained in the pretreated biomass to monosaccharide such as glucose and xylose.

In the process, when adding cellulase enzyme complex to the solid obtained at the step 3 and performing saccharification, water may be added, but to obtain a high concentration of sugar solution after saccharification, it is preferred to control its amount. Thus, a ratio of water to the solid in the enzymatic hydrolysis before pretreatment of the solid is preferably from 1:3 to 1:10 in weight ratio on biomass dry weight basis.

For enzymatic hydrolysis of the pretreatment product, cellulase enzyme complex containing hemicellulose is used, and its example includes a mixed preparation of Celluclast® 1.5 L or Celluclast® conc BG and Novozyme™ 188, a mixture of Cellic CTec2 and Cellic HTec2 or a mixture of Cellic CTec3 and hemicellulose, a mixed preparation of Celluzyme®, Cereflo® and Ultraflo® (Novozymes, Denmark), a mixture of Acellerase™, Laminex® and Spezyme® (Genencor Int.), and Rohament® (Rohm GmbH). As the liquid hot water pretreatment product contains a small amount of hemicellulose, hemicellulose may be added to accelerate the hydrolysis rate, and a mix ratio of cellulase and hemicellulose is preferably from about 9:1 to about 10:0. Also, an amount of cellulase enzyme complex used per 1 g dry weight of biomass is preferably from 0.001 g to 0.5 g.

The enzymatic hydrolysis is maintained under the condition in which the hydrolysis enzyme shows maximum activity, that is, in the case of a mixture of Cellic CTec2 and Cellic HTec2, it is preferably maintained at pH of 4.8 to 5.2 and temperature of 50±1° C., and in the absence of contamination by microorganisms, saccharification preferably lasts for 24 hours to 96 hours or longer.

The pretreated liquid that remains in the solid of the present disclosure in part and entered the enzymatic hydrolysis process contains materials such as xylose and xylooligosaccharides that can partially inhibit the activity of the cellulose hydrolysis enzyme, so the sugar yield may be slightly reduced in enzymatic hydrolysis. Thus, the present disclosure may use the following two methods that have been disclosed to increase the sugar yield in the enzymatic hydrolysis of the pretreatment product. One is a method which adds polyethyleneglycol (PEG) known to increase activity of cellulose hydrolysis enzyme in enzymatic hydrolysis (see U.S. Pat. No. 7,972,826). This may enhance sugar yields by inhibiting enzyme from irreversibly binding to lignin on the surface of the pre-treated product. However, to prevent PEG from remaining as impurities when producing fermentable sugar, PEG having a molecular weight of 30,000 or higher is used for recovery by a separation membrane process after saccharification. The other is a method of adding a particular clay mineral in a small amount during liquid hot water pretreatment or enzymatic hydrolysis (see Korean Patent Publication No. 2012-73087 and WO/2012/087068). This method increases the sugar yield without washing the pretreated solid with water and does not contain any additive in the produced sugar solution, and is thus advantageous in producing fermentable sugar.

In the method of the present disclosure, the fifth step, i.e., the sugar solution recovery step is a step of recovering a sugar solution from the saccharification product obtained at the step 4 through repeated processes of solid-liquid separation and extraction. In the recovery step, methods such as continuous centrifugal separation, filter press, batch-type centrifugal separation, and screw press may be used. Taking batch-type recovery process as an example, centrifugal separation of the saccharification product is performed to recover a supernatant, and the saccharification residue is diluted with water of the same volume, followed by centrifugal separation, to recover a sugar solution, and this process is repeated 3 to 5 times, and then 99% or more of sugar produced by enzymatic hydrolysis may be recovered.

In the method of the present disclosure, the sixth step, i.e., the fermentable sugar obtaining step is a step of obtaining fermentable sugar by filtration, concentration and impurity removal from the sugar solution obtained at the step 5. The final sugar concentration of the sugar solution obtained at the step 5 is diluted during recovery of sugar, and reduces to about 50% of the initial concentration, i.e., about 60 g/L to 150 g/L, and the sugar solution of this low concentration may increase up to 30% or higher of sugar concentration through a concentration process using membrane separation technique. The concentration process may be performed using reverse osmosis filtration and nanofiltration widely known in the art. Also, to recycle the enzyme contained in the sugar solution, it may be recovered using ultrafiltration, or it may be removed using solid-liquid separation technique after heating to denature it and turning it into a precipitate.

In the present disclosure, to preventing the fermentable sugar from going bad by microorganism contamination while storage, the sugar solution prepared at a high glucose concentration of 30% or higher also contains a low concentration of organic acids such as acetic acid and formic acid produced by hydrolysis of hemicellulose, a trace of furfural and HMF, phenolic compounds produced by degradation of lignin and a small amount of inorganic salts derived from biomass. However, the concentration of these impurities except sugar is very low, so when the sugar solution is diluted at the concentration at which metabolite is normally produced, it does not greatly hinder the growth of many industrial microbes such as *E. coli* and yeast used as strains widely used to produce many chemicals and biofuel, *Clostridium acetobutylicum* and *Clostridium beijerinckii* used to produce butanol and acetone, *Lactococcus lactis* and *Lactobacillus* sp. mainly producing lactic acid, and *Corynebacterium glutamicum* primarily used to produce amino acid.

In the method of the present disclosure, the seventh step, i.e., the alcohol fermentation step is a step of fermenting the fermentable sugar obtained at the step 6 using an ethanologen. The fermentation step may be performed by a method known in the art of producing ethanol from glucose. An example of the ethanologen includes, but is not limited to, *Saccharomyces cerevisiae, Escherichia coli, Clostridium beijerinckii, Clostridium acetobutylicum*, and *Zymomonas mobilis*. In one specific example of the present disclosure, the step 7 may be performed by adding a yeast extract and peptone to the fermentable sugar obtained at the step 6, inoculating with *Saccharomyces cerevisiae* as an ethanologen and cultivating at 30±1° C. under anaerobic conditions. The cultivation may be performed by batch-type or continuous-type.

An example of lignocellulosic biomass that can be used as a raw material in the bioethanol production method of the present disclosure includes herbaceous biomass and woody biomass. However, in addition to the lignocellulosic biomass, biomass containing cellulose as a main source of sugar may be used without limit, for example, algal biomass including microalgae and sea algae. Examples of herbaceous biomass include trunk, frond, and empty fruit bunch of oil palm, sunflower stalks, rice straw, barley straw, wheat straw, corn stover, reed, miscanthus, switchgrass, rape stalks, sweet sorghum stalks, sorghum stalks, and reedmace, and examples of woody biomass include yellow poplar, willow, acacia, eucalyptus, and spruce, but are not limited thereto.

The method for producing bioethanol using lignocellulosic biomass of the present disclosure as a raw material is a simplest method, and may fractionate biomass to prepare a high concentration of sugar solution at high yields, and produce bioethanol therefrom at high yields, thereby maximizing the use efficiency of biomass.

<A Method for Producing Fermentable Sugar with Lignocellulosic Biomass Raw Material in which a Microbial Inhibitor was Removed>

The present disclosure provides a method for producing fermentable sugar from lignocellulosic biomass in which acetic acid was removed, the method including the steps of:

1) adding water to coarsely ground or powdery lignocellulosic biomass and performing liquid hot water pretreatment, and performing solid-liquid separation of the obtained pretreatment product to obtain a solid;

2) adding an aqueous alkali solution warmed at room temperature to 100° C. or less to the solid obtained at the step 1), mixing them and dehydrating to recover the solid; and 3) adding a cellulose hydrolysis enzyme to the solid obtained at the step 2) to perform enzymatic hydrolysis.

The technical subject matter of the method for producing fermentable sugar according to the present disclosure is characterized by producing fermentable sugar widely used for fermentation of many industrial microbes with the minimized content of microbial growth inhibitors such as acetic acid through a series of processes including (i) a liquid hot water pretreatment of biomass and solid-liquid separation step, (ii) an alkaline water washing step, and (iii) an enzymatic hydrolysis step.

The term "fermentable sugar" as used herein represents sugar that can be used for fermentation of microorganisms, and is distinguished from a "sugar solution" that collectively refers to all solutions containing sugar.

In the method for producing fermentable sugar in which most of the microbial inhibitors such as acetic acid is removed according to the present disclosure, the first step is a step of performing solid-liquid separation of a pretreatment product obtained by liquid hot water pretreatment of lignocellulosic biomass to obtain a solid containing a minimum of liquid (liquid hot water pretreatment and solid-liquid separation step).

As the pretreated liquid that is acidic is removed as much as possible at this step, the amount of chemicals consumed in a subsequent washing step using an aqueous alkali solution may be reduced.

The liquid hot water pretreatment step may be performed by a method well known in the art, and for example, liquid hot water pretreatment of lignocellulosic biomass may be performed at 160 to 230° C. for 0.001 to 60 minutes. To separate and remove an acidic liquid from the pretreatment product obtained through the above process, all solid-liquid separation methods commonly used in the art may be used, and its example includes centrifugal separation, rotary dehydration, suction filtration and pressure filtration.

In the method of the present disclosure, the second step is a step by adding an aqueous alkali solution to the pretreated solid obtained at the first step, mixing them, dissolving acetic acid in the liquid remaining in the pretreated solid and acetyl group present in unreacted state in the solid, and removing the liquid containing acetic acid by solid-liquid separation (alkaline water washing step).

The washing process of the pretreated solid by this aqueous alkali solution is core technology of the present disclosure, and its main object is to separate and remove acetyl groups that are not hydrolyzed even after pretreatment of biomass and still remain. In this instance, an available aqueous alkali solution is a solution in which a base is dissolved or suspended in water, and for example, the base may be selected from the group consisting of calcium hydroxide, potassium hydroxide, sodium hydroxide and mixtures thereof, and the aqueous alkali solution is not particularly limited if it is prepared to exhibit alkalinity of pH of 11 or higher when mixed with the biomass pretreatment product from which acetic acid is to be removed.

To remove acetic acid remaining in the pretreatment product at this step, first, after preparing a high concentration of aqueous alkali solution or suspension by dissolving or suspending the base in water, it is desirable to add it to the pretreated solid and mixing them, and in this instance, alkali concentration, temperature and reaction time in the reaction system have a close relationship with each other, and can be controlled within a predetermined range.

The aqueous alkali solution added to the pretreated solid preferably has an initial concentration at which the pH 11 or higher is maintained even after neutralizing the free acetic acid in the solid to maintain its reactivity to acetyl group that is chemically bonded to hemicellulose, and for example, a concentration at which the pH is from 11.5 to 14 when mixed with the pretreated solid. When the initial concentration of the aqueous alkali solution is as high as the pH is close to 14, the removal efficiency of acetyl group in the pretreated solid is high. However, due to an increase of water needed to adjust the pH to weak acidity or an amount of acid used as a neutralizing agent to maximize the enzyme activity at the enzymatic hydrolysis step after removal of acetic acid, causing a reaction with an addition of the aqueous alkali solution of a minimum concentration required for acetyl group removal is effective for reducing an amount of water and chemicals consumed.

When removing acetic acid by washing the pretreated solid with the aqueous alkali solution, in the case where the alkali concentration and the washing time is constant, as the temperature of the reaction system increases, the removal rate of acetic acid increases. Also, if the temperature of the reaction system increases, the concentration of the aqueous alkali solution used reduces, and the washing time reduces. For example, in the case where acetic acid is extracted and removed by washing for 2 minutes from the pretreatment product obtained by performing liquid hot water pretreatment of 1 g sunflower stalks at 190° C. for 5 minutes, the extraction efficiency for the remaining acetyl group in the pretreatment product at 80° C. using an aqueous solution of calcium hydroxide at the same saturated concentration is higher about twice than the extraction efficiency at 60° C. However, if the temperature of the aqueous alkali solution exceeds 100° C., a special apparatus is required to maintain the pressure. However, once the pH of the reaction system is above 11, the removal reaction of acetyl groups takes place even at the room temperature. So the washing temperature is preferably set in the range of the room temperature to 100° C. or less. Also, to reduce an amount of reagents consumed and the washing time, it is more desirable to select, for example, the temperature of 80° C. to 95° C. within this range, and in the case where treatment is performed at the temperature, a preferred treatment time is from 0.001 minutes to 60 minutes.

An amount of the aqueous alkali solution added to the pretreated solid is not particularly limited if it is above an amount at which uniform mixing with the pretreated solid is achieved, but it is desirable to control the amount in consideration of efficiency and costs for removing acetate already produced after reaction by solid-liquid separation or washing. For example, an available amount of the aqueous alkali solution added is an amount corresponding to 20 times of the pretreated solid weight (e.g., an amount 1 to 20 times as much based on the total weight of the pretreated solid) above the volume (water content about 50%) at which liquid of the reaction system is removed even in part by solid-liquid separation with such as screw press or centrifugal dehydrator after mixing and reacting the pretreatment product with the aqueous alkali solution. Subsequently, if necessary, to further remove the extracted acetic acid and the aqueous alkali solution from the pretreatment product, a washing process using water may be added, but may be controlled according to a usage amount of the aqueous alkali solution.

In the method of the present disclosure, the third step, i.e., the enzymatic hydrolysis step is a step of adding a cellulose hydrolysis enzyme to the pretreated solid from which most of acetic acid obtained at the second step is removed and performing enzymatic hydrolysis (enzymatic hydrolysis step).

In this step, a process of converting cellulose and hemicellulose contained in the pretreated biomass to monosaccharide such as glucose and xylose is not greatly different from a method commonly known in the art. According to one embodiment of the present disclosure, after controlling the pH in the range of 4.5 to 5.5 by adding acids to the pretreated solid from which most of acetic acid is removed, a cellulose hydrolysis enzyme is added. The cellulose hydrolysis enzyme may be selected from the group consisting of Cellic CTec2, Cellic HTec2 and mixtures, and after adding the enzyme, enzymatic hydrolysis may be performed by stirring for 24 to 72 hours while maintaining 50±1° C. and pH 5.0±0.1.

The enzymatic hydrolysis material obtained through the enzymatic hydrolysis step leads to production of fermentable sugar in which acetic acid was removed, for example, through centrifugal separation.

The fermentable sugar produced according the method of the present disclosure is characterized in that the content of acetic acid is reduced by ½ or less as compared to a sugar solution prepared without removing acetic acid after pretreatment. According to one embodiment of the present disclosure, the acetic acid yield of fermentable sugar produced from sunflower stalks is reduced from 0.51 g to 0.09 g per 100 g biomass, and the acetic acid yield of fermentable sugar produced from reed is reduced from 0.25 g to 0.05 g, all reduced to ⅕ or less (Examples 2 and 3).

The fermentable sugar produced by the method of the present disclosure contains acetic acid produced by pretreatment and enzymatic hydrolysis of biomass, furfural, HMF, phenolic compounds produced by degradation of lignin, and inorganic salts derived from biomass at a very low concentration, and is thus suitable for fermentation of many industrial microbes such as *E. coli* and yeast used as strains widely used to produce many chemicals and biofuel, *Clostridium acetobutylicum* and *Clostridium beijerinckii* used to produce buthanol and acetone, *Lactococcus lactis* and *Lactobacillus* sp. involved mainly in the production of lactic acid, *Corynebacterium glutamicum* primarily used to produce amino acid, and *Zymomonas mobilis* commonly used to produce ethanol. Particularly, it is useful for cultivation of strains being affected to the concentration of acetic acid very sensitively in the growth, and such strains include yeast (*Saccharomyces cerevisiae*).

Therefore, the present disclosure provides a method for fermentation of microorganisms using fermentable sugar in which acetic acid was removed as produced according to the method of the present disclosure.

The lignocellulosic biomass that can be used as a raw material in the method of the present disclosure includes both herbaceous biomass and woody biomass. Examples of herbaceous biomass include trunk, frond, and empty fruit bunch of oil palm, sunflower stalks, rice straw, barley straw, wheat straw, corn stover, reed, miscanthus, switchgrass, rape stalks, sweet sorghum stalks, sorghum stalks, and reedmace, and examples of woody biomass include yellow poplar, willow, acacia, eucalyptus, and spruce, but are not limited thereto.

The method for producing fermentable sugar according to the present disclosure removes many microbial growth inhibitors while at the same time, minimizing the content of acetic acid in fermentable sugar produced finally when producing fermentable sugar, in principle, using hydrolysis technique by an acid catalyst, for example, liquid hot water pretreatment, and thus, is useful in preparing a sugar solution for fermentation using lignocellulosic biomass as a raw material.

<A Method for Producing Fermentable Sugar Having Reduced Toxicity of Acetic Acid from Lignocellulosic Biomass>

The present disclosure provides a production method of fermentable sugar having reduced toxicity of acetic acid, including the steps of:

1) performing liquid hot water pretreatment of lignocellulosic biomass to produce a pretreatment product for enzymatic hydrolysis; and 2) adding a cellulose hydrolysis enzyme to the pretreatment product obtained at the step 1, and adding an alkali reagent including a base with at least two hydroxyl groups in a molecule, having a dissolution constant ($pKa_2$) of 8.0 or more for a second acetyl group of acetate, to perform enzymatic hydrolysis.

The technical subject matter of the method for producing fermentable sugar according to the present disclosure is characterized by producing fermentable sugar widely used for fermentation of many industrial microbes with the minimum content of microbial growth inhibitors such as acetic acid through a series of processes including 1) a step of producing a pretreatment product for enzymatic hydrolysis by liquid hot water pretreatment of biomass, and 2) a step of performing enzymatic hydrolysis using, as a neutralizing agent, an alkali reagent including a base with at least two hydroxyl groups in a molecule, having a dissolution constant ($pKa_2$) of 8.0 or more for a second acetyl group of acetate.

The production and dissolution processes of acetate are shown in the following reaction formula 1.

[Reaction Formula 1]

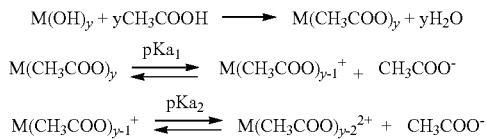

In the above formula,
M is calcium, barium or magnesium, and
y is the number of hydroxyl groups.

In the method for producing fermentable sugar having greatly reduced toxicity of acetic acid according to the present disclosure, the first process is a step of producing a pretreatment product for enzymatic hydrolysis by liquid hot water pretreatment of biomass.

The pretreatment product for enzymatic hydrolysis may be selected from the group consisting of a) both a liquid and a solid obtained by performing liquid hot water pretreatment of lignocellulosic biomass; b) a solid obtained by solid-liquid separation after liquid hot water pretreatment of lignocellulosic biomass; and c) a pretreatment product dehydrated after washing the solid obtained by solid-liquid separation after liquid hot water pretreatment of lignocellulosic biomass with water or an aqueous alkali solution.

Specifically, the pretreatment product for enzymatic hydrolysis may be produced by three methods as below. The first method of producing a pretreatment product for enzymatic hydrolysis uses, in enzymatic hydrolysis, all the entire pretreatment product including both a pretreated liquid and a solid obtained by liquid hot water pretreatment of lignocellulosic biomass. In this instance, acetic acid included in the pretreated liquid and acetyl groups remaining in unreacted state in the pretreated solid are both converted to acetate through a neutralization reaction by an alkali reagent with at least two hydroxyl groups in a molecule in the enzymatic hydrolysis process.

The second method of producing a pretreatment product for enzymatic hydrolysis is for removing a maximum of liquid through solid-liquid separation of the pretreatment product obtained by liquid hot water pretreatment of lignocellulosic biomass. As the pretreated liquid in acidic state after pretreatment is removed as much as possible, an amount of acetic acid remaining is reduced, and an amount of chemicals spent at a subsequent enzymatic hydrolysis step may be reduced. In this instance, all solid-liquid separation methods commonly used in the art may be used to separate and remove an acidic liquid from the pretreatment product, and its example includes centrifugal separation, centrifugal dehydration, suction filtration and pressure filtration.

The third method of producing a pretreatment product for enzymatic hydrolysis is for removing all the remaining acetic acid by dewatering after washing the solid obtained by solid-liquid separation after liquid hot water pretreatment of lignocellulosic biomass with water or an aqueous alkali solution.

In the present disclosure, the liquid hot water pretreatment step may be performed according to a method well known in the art, and for example, liquid hot water pretreatment of lignocellulosic biomass may be performed at 160 to 230° C. for 1 to 60 minutes.

In the method of the present disclosure, the second step is a step of transferring the pretreatment product for enzymatic hydrolysis obtained at the first step to a saccharification tank, adding a cellulose hydrolysis enzyme to perform hydrolysis, and performing enzymatic hydrolysis while maintaining the temperature, pH and stirring speed where the activity of an enzyme is at maximum. Here, as an alkali reagent for pH control added to maintain a constant pH, the use of an aqueous alkali solution or suspension including a base with at least two hydroxyl groups in a molecule, having a dissolution constant ($pKa_2$) of 8.0 or more for a second acetyl group of alkali acetate is core technology of the present disclosure.

At the enzymatic hydrolysis step, the temperature and the stirring speed at which the activity of the enzyme is at maximum may vary depending on the enzyme, and is not particularly limited, but for example, in the case where a mixture of Cellic CTec2 and Cellic HTec2 from Novozymes (Denmark enzyme production company) is used, the temperature may be from 45 to 70° C., and the stirring speed may be from 50 to 200 rpm.

The fermentable sugar produced according to the method of the present disclosure may contain acetic acid converted to a conjugate base. Taking calcium diacetate [Ca(CH$_3$COO)$_2$] of the above reaction formula 1 as an easiest example of the conjugate base, a description is provided. At the second step of the present disclosure, i.e., the step of enzymatic hydrolysis of biomass liquid hot water pretreatment product, when a calcium hydroxide aqueous solution or calcium hydroxide suspension is used to maintain an optimum pH of the enzyme in the range of pH 4.5 to pH 5.5, acetic acid produced by hydrolysis of hemicellulose is neutralized to produce calcium diacetate. While a first dissolution constant (pKa$_1$=6.3) of this calcium diacetate belongs in the acidic region, a second dissolution constant (pKa$_2$=9.6) belongs in the alkaline region above the neutral region. Acetic acid anions dissociated in the first acidic region enter mitochondria of microorganism and disturb energy metabolism, and shows toxicity, but calcium acetate cations having a second acetyl group are hardly dissociated at an acidic or neutral pH, and in fact, they cannot act as an acetyl group. Thus, analysis reveals that the fermentable sugar produced according to the method of the present disclosure contains the same concentration of acetic acid as fermentable sugar ordinarily produced, while there is an effect that reduces the concentration of acetic acid harmful to microorganisms less than about half when subsequently cultivating industrial microbes using it as a carbon source.

The alkali reagent that can be used in the method of the present disclosure is not particularly limited if when converted to acetate, it is a base with at least two hydroxyl groups in a molecule, having a dissolution constant (pKa$_2$) of 8.0 or more for a second acetyl group of acetate, and has no toxicity to microorganisms at the pH round the neutral region. This base may be directly fed and used for neutralization of a sugar solution after it becomes a fine powder form, or may be used as an aqueous alkali solution in which the base is dissolved in water or a colloidal suspension in which the base is finely ground by wet mill. Examples of the base include calcium hydroxide, barium hydroxide and magnesium hydroxide, and preferably calcium hydroxide.

Calcium hydroxide may be prepared and used in the form of an aqueous solution, but due to a low water solubility (0.17 g/100 ml, 25° C.), if an excessive amount of aqueous solutions is used, the concentration of the sugar solution may be remarkably reduced. To prevent this, for example, it is more desirable to prepare and use calcium hydroxide in the form of a high concentration of colloidal suspension after fine grinding with an average diameter of 0.001 to 10 μm. In this instance, the concentration of calcium hydroxide in the suspension may be, for example, from 1% (w/w) to 20% (w/w).

The enzymatic hydrolysis product obtained through the enzymatic hydrolysis step leads to production of fermentable sugar containing acetic acid having reduced toxicity by recovering a sugar solution through separation processes such as centrifugal separation.

Using the fermentable sugar produced by method of the present disclosure, half or more of acetic acid produced by pretreatment and enzymatic hydrolysis of biomass does not dissociate under an ordinary fermentation condition and, therefore, does not cause acidity. Thus, the fermentable sugar according to the present disclosure is suitable for fermentation of many industrial microbes such as *E. coli* and yeast used as strains widely used to produce many chemicals and biofuel, *Clostridium acetobutylicum* and *Clostridium beijerinckii* used to produce buthanol and acetone, *Lactococcus lactis* and *Lactobacillus* sp. involved mainly in the production of lactic acid, *Corynebacterium glutamicum* primarily used to produce amino acid, and *Zymomonas mobilis* commonly used to produce ethanol. Particularly, it is useful for cultivation of strains being affected to the concentration of acetic acid very sensitively in the growth, and such strains include yeast (*Saccharomyces cerevisuae*).

Therefore, the present disclosure provides a method for fermentation of microorganisms using fermentable sugar having reduced toxicity of acetic acid as produced according to the method of the present disclosure.

The lignocellulosic biomass that can be used as a raw material in the method for producing fermentable sugar includes both herbaceous biomass and woody biomass. Examples of herbaceous biomass include trunk, frond, and empty fruit bunch of oil palm, sunflower stalks, rice straw, barley straw, wheat straw, corn stover, reed, miscanthus, switchgrass, rape stalks, sweet sorghum stalks, sorghum stalks, and reedmace, and examples of woody biomass include yellow poplar, willow, acacia, eucalyptus, and spruce, but are not limited thereto.

The method for producing fermentable sugar according to the present disclosure may reduce toxicity of acetic acid without removing acetic acid produced by hydrolysis of hemicellulose, and thus, is useful in preparing a sugar solution for fermentation using lignocellulosic biomass as a raw material.

<A Method for Producing Microbial Metabolite from Lignocellulosic Biomass Containing Starch>

In one embodiment of the present disclosure according to the object, there is provided a method for producing microbial metabolite from lignocellulosic biomass containing starch, including the steps of 1) performing liquid hot water pretreatment of ground lignocellulosic biomass containing starch using steam or water under the following condition: a) a temperature range of 170° C. to 230° C.; and b) a reaction time at which the yield of hemicellulose sugar produced at the step 2) is at maximum; 2) saccharifying the entire pretreatment product using cellulase or cellulase enzyme complex without solid-liquid separation; and 3) adding microorganisms to the saccharification product to perform fermentation.

In another embodiment of the present disclosure according to the object, there is provided a method for producing microbial metabolite from lignocellulosic biomass containing starch, including the steps of: 1) gelatinizing and swelling ground lignocellulosic biomass containing starch using boiling water or steam; 2) adding starch hydrolase to the gelatinized and swollen biomass meal to hydrolyze the starch; 3) adding microorganisms to the hydrolyzed biomass meal to perform fermentation; 4) performing liquid hot water pretreatment of the fermented biomass meal using steam or water under the following condition: a) a temperature range of 170° C. to 230° C., and b) a reaction time at which the yield of hemicellulose sugar produced at the step 5) is at maximum; 5) saccharifying the entire pretreatment product using cellulase or cellulase enzyme complex without solid-liquid separation; and 6) adding microorganisms to the saccharification product to perform fermentation.

When producing metabolite with microorganism such as bioethanol or lactic acid from lignocellulosic biomass containing starch, the present disclosure provides a method which performs enzymatic hydrolysis and microbial fermentation or simultaneous saccharification and co-fermentation after liquid hot water pretreatment under not severe conditions in which the yield of hemicellulose sugar is at maximum, without extracting or recovering starch beforehand, thereby maximizing a microbial metabolite conversion ratio of carbohydrate in biomass while inhibiting the loss or degradation reaction of sugar to the minimum during physicochemical pretreatment of biomass.

In one embodiment of the present disclosure, the method for producing microbial metabolite from lignocellulosic biomass containing starch according to the present disclosure (method 1) includes the steps of 1) performing liquid hot water pretreatment of ground lignocellulosic biomass containing starch using steam or water under the following condition: a) a temperature range of 170° C. to 230° C. and b) a reaction time at which the yield of hemicellulose sugar produced at the step 2) is at maximum; 2) saccharifying the entire pretreatment product using cellulase or cellulase enzyme complex without solid-liquid separation; and 3) adding microorganisms to the saccharification product to perform fermentation.

In another embodiment of the present disclosure, the method for producing microbial metabolite from lignocellulosic biomass containing starch according to the present disclosure (method 2) includes the steps of 1) gelatinizing and swelling ground lignocellulosic biomass containing starch using boiling water or steam; 2) adding starch hydrolase to the gelatinized and swollen biomass meal to hydrolyze the starch; 3) adding microorganisms to the hydrolyzed biomass meal to perform fermentation; 4) performing liquid hot water pretreatment of the fermented biomass meal using steam or water under the following condition: a) a temperature range of 170° C. to 230° C., and b) a reaction time at which the yield of hemicellulose sugar produced at the step 5) is at maximum; 5) saccharifying the entire pretreatment product using cellulase or cellulase enzyme complex without solid-liquid separation; and 6) adding microorganisms to the saccharification product to perform fermentation.

The term "lignocellulosic biomass containing starch" as used in the method of the present disclosure represents lignocellulosic biomass containing starch as one material as well as cellulose, hemicellulose and lignin in lignocellulosic biomass. Specific examples of the lignocellulosic biomass containing include trunk and frond of palm trees such as oil palms, sago palms; food crops having starch rich roots containing cellulose and hemicellulose and lignin as materials, such as cassava and sweet potato; and by-products produced during cereal polishing, such as rice bran, wheat bran, corn bran and barley bran.

The term "microorganism" as used in the method of the present disclosure represents strains for fermentation used in the biochemical industry to produce microbial metabolites such as alcohols including ethanol, propanol, propandiol, butanol, and butandiol; ketones including acetone and lactone; amino acids including lysine; organic acids including acetic acid, lactic acid, butyric acid, fumaric acid, maleic acid, succinic acid, gamma-aminobutyric acid, aminovaleric acid, and glutaric acid; benzene; or hydrocarbon by using sugars, for example, glucose or fructose, as a carbon source. This microorganism includes, for example, genus *Escherichia*, genus *Sacharomyces*, genus *Serratia*, genus *Lactobacillus*, genus *Lactococcus*, genus *Leuconostoc*, genus *Corynebacterium*, genus *Brevibacterium* or genus *Clostridium*, and is not limited to a particular type provided that it provides metabolite useful for humans.

The term "microbial metabolite" as used herein represents a biochemical material that can be produced by microorganisms using sugars (e.g., glucose and so on) as a carbon source, and its example includes alcohols including ethanol, propanol, propandiol, butanol, and butandiol; ketones including acetone and lactone; amino acids including lysine; organic acids including acetic acid, lactic acid, butyric acid, fumaric acid, maleic acid, succinic acid, gamma-aminobutyric acid, aminovaleric acid, and glutaric acid.

The term "starch hydrolysis" as used herein represents hydrolysis of starch contained in biomass using starch hydrolase (or amylase enzyme complex), and there is no big difference from hydrolysis of starch in corn or potato. However, because each biomass contains different types of carbohydrates at different ratios, the starch hydrolase used may be a bit different in composition and addition ratio. The starch hydrolase include, but is not limited to, for example, α-amylase, β-amylase, amyloglucosidase, invertase or mixtures thereof, and many starch hydrolases commonly used in the art may be used. The starch hydrolysis process first performs hydrolysis of starch contained in biomass to produce glucose that is supplied as a source of carbon in the subsequent microbial fermentation. This subsequent physicochemical pretreatment facilitates the degradation of hemicellulose and lignin contained in lignocellulosic biomass. The process includes suspending biomass powder in water, adding starch hydrolase, and stirring for a predetermined time at 30 to 70° C., preferably 50° C. while uniformly maintaining the pH. The process may further include a heating sterilization process before adding an enzyme to the biomass powder suspension to inhibit the propagation of unwanted microorganisms during hydrolysis, and it is possible to use a larger amount of starch hydrolases not to give the time for propagation of microorganisms.

The term "liquid hot water pretreatment of biomass" as used herein refers to a process which adds steam or water to biomass to make cellulose or hemicellulose easily hydrolyzed in a saccharification process of biomass, and performs thermochemical treatment, and represents a step prior to a process for converting to monosaccharide by cellulose hydrolysis enzymes (enzymatic hydrolysis), or simultaneous saccharification and co-fermentation process using enzymes and fermentation strains together. This step is a process which first thermochemically hydrolyzes and dissolves hemicellulose in biomass to increase the reactivity of cellulose to hydrolysis enzymes.

The term "enzymatic hydrolysis" as used herein represents a process of converting cellulose and hemicellulose contained in pretreated biomass to monosaccharide such as glucose and xylose using a so-called cellulase enzyme complex.

The term "cellulase enzyme complex" as used herein refers to a hemicellulose hydrolysis enzyme, and an enzyme complex containing starch hydrolase as well as a cellulose enzyme complex, and serves to convert carbohydrate, cellulose and hemicellulose in polymer form to monosaccharide. Examples of the enzyme include a mixed preparation of Celluclast® 1.5 L or Celluclast® conc BG and Novozyme™ 188, a mixed preparation of Cellic CTec2 and Cellic HTec2, a mixed preparation of Cellic CTec3 and Cellic HTec2, a mixed preparation of Celluzyme®, Cereflo®, and Ultraflo® (Denmark Novozymes), a mixed preparation of Accellerase™, Laminex®, and Spezyme® (Genencor Int.), or Rohament® (Rohm GmbH). The starch hydrolase, cellulose hydrolysis enzyme, and cellulase enzyme complex containing hemicellulose hydrolysis enzyme such as the above are being produced by many domestic and foreign protein production companies including Denmark, USA, and so on, and they are commercially available.

In the method of the present disclosure, enzymatic hydrolysis and fermentation may be simultaneously performed. That is, the step 2 and step 3 of the method 1 of the present disclosure, and the step 2 and step 3 and the step 5 and step 6 of the method 2 of the present disclosure may be simultaneously performed, and simultaneous saccharification and co-fermentation may be applied.

In the method of the present disclosure, as the lignocellulosic biomass containing starch is ground fine, the rate and efficiency of hydrolysis by starch hydrolase or invertase becomes higher. Also, even though biomass is coarsely ground, once starch is gelatinized and swollen during sterilization using boiling water, the rate and efficiency of hydrolysis by enzymes may be higher. However, for improving the reaction rate and the yield and availability in microbial fermentation, and favorable feeding into a pretreatment apparatus in a subsequent pretreatment process of biomass, biomass is preferably crushed or ground to a size less than or equal to 0.1 mm to 50 mm in diameter.

In the method for efficiently producing microbial metabolite from lignocellulosic biomass containing starch according to the present disclosure, the step 1 of the method 1 is a step of performing liquid hot water pretreatment of ground lignocellulosic biomass containing starch using steam or water to produce a pretreatment product. In this instance, a portion of hemicellulose in biomass is hydrolyzed and dissolved in water, resulting in a higher surface area of biomass, and as a consequence, higher hydrolysis efficiency of cellulose in subsequent enzymatic hydrolysis. Although a large amount of water participating in hydrolysis reaction of hemicellulose is not required, a sufficient amount of water for thoroughly wetting biomass is required to transmit heat evenly and cause a reaction uniformly. Thus, a ratio of biomass and water is preferably from 1:2 to 1:20, and when considering uniform mixing during liquid hot water pretreatment and a recovery cost of metabolite after subsequent fermentation using microorganisms, 1:5 to 1:15 is more desirable.

The liquid hot water pretreatment of lignocellulosic biomass containing starch according to the present disclosure is a process of steaming biomass using high temperature steam or water, and the present disclosure is characterized by liquid hot water pretreatment under the following condition: a) a temperature range of 170° C. to 230° C. and b) a reaction time in which the yield of hemicellulose sugar produced at the step 2) is at maximum. The liquid hot water pretreatment condition is limited to, a) a temperature range of 170° C. to 230° C., and b) a reaction time in which an amount of hemicellulose sugar produced by enzymatic hydrolysis using the entire pretreatment product as a substrate after liquid hot water pretreatment, that is, amounts of xylose and galactose, arabinose and mannose are at maximum. This liquid hot water pretreatment condition includes, for example, heating treatment at 180° C. for about 20 to 30 minutes, 190° C. for about 10 minutes, 200° C. for about 5 minutes in the batch-type pretreatment of palm trunk, followed by quick cooling.

In the present disclosure, the most suitable liquid hot water pretreatment condition for lignocellulosic biomass containing starch is a complex function of the pretreatment temperature and the reaction time, and the higher pretreatment temperature the shorter reaction time. That is, in the case where liquid hot water pretreatment is performed at low temperature within the temperature range of 170° C. to 230° C. as described in the present disclosure, the reaction time in which the hemicellulose sugar yield is at maximum becomes longer, and in the case where liquid hot water pretreatment is performed at high temperature, the reaction time in which the hemicellulose sugar yield is at maximum becomes shorter. For example, as shown in FIG. 1, in the case of palm trunk biomass, when liquid hot water pretreatment is performed at 180° C., the reaction time in which the hemicellulose sugar yield is at maximum is from about 20 to 30 minutes, for 190° C., the reaction time is about 10 minutes, for 200° C., the reaction time about 5 minutes, and particularly, when liquid hot water pretreatment is performed at 180° C. for about 20 minutes, the hemicellulose sugar yield is highest (see FIG. 1). This pretreatment condition may be changed depending on the type of lignocellulosic biomass containing starch, and this condition mentioned above is the liquid hot water pretreatment condition of lignocellulosic biomass containing starch in the present disclosure.

When liquid hot water pretreatment is performed at a particular temperature set as a pretreatment temperature for variable reaction time, the yield of hemicellulose sugar produced by subsequent enzymatic hydrolysis has a tendency to increase up to any time and subsequently reduce sharply. In this instance, when it goes beyond the reaction time in which the yield of hemicellulose sugar is at maximum, lignin degradation products are rapidly produced together with production of further degraded products such as furfural which inhibit the microbial growth by further degradation of xylose. Thus, when saccharification using a cellulase enzyme complex is performed after liquid hot water pretreatment of biomass under the above condition, the yield of hemicellulose sugar is maximized, and at the same time, production of further degraded products and production of lignin degradation products is inhibited to the minimum, making it suitable for production of metabolite by subsequent microbial fermentation. In contrast, if liquid hot water pretreatment condition is more severe, production of further degraded products of carbohydrates and production of lignin degradation products increases, resulting in unfavorable microbial growth or fermentation in subsequent enzymatic hydrolysis and microbial fermentation.

In the method of efficiently producing microbial metabolite from lignocellulosic biomass containing starch according to the present disclosure, the step 2 of the method 1 is a step of saccharifying the entire biomass pretreatment product obtained at the step 1 using cellulase or cellulase enzyme complex without solid-liquid separation. The biomass pretreatment product obtained at the step 1 contains not only water-soluble substances inherently contained in biomass such as protein and inorganic salts, but also water-soluble starch partially solubilized from starch, xylose, xylooligosaccharide, acetic acid, and arabinose produced by hydrolysis of hemicellulose and a trace of lignin degradation products by thermal degradation of lignin. The step 2 is a process of adding starch and cellulose hydrolysis enzyme hereto and performing enzymatic hydrolysis. According to conventional bioethanol production research, the pretreated solid is separated and recovered from slurry by solid-liquid separation after pretreatment of biomass, and then is saccharified by enzymes, but the present disclosure is characterized in that all the pre-treated products produced after pretreatment are used in enzymatic hydrolysis. This is because the liquid obtained after pretreatment contains a large amount of starch or sugar, and little microbial growth inhibitor. Thereby, both starch and sugar contained in biomass can be used in microbial fermentation after saccharification.

In a method of treating lignocellulosic biomass containing starch according to the present disclosure, the step 3 of the method 1 is a step of adding microorganisms to the biomass saccharification product obtained at the step 2 and performing fermentation. The fermentation using microorganisms at this step is not greatly different from ordinary fermentation using target strains, and thus, a special condition is not defined. However, because protein substances already contained in biomass may act as a nutrient source in the fermentation of microorganisms, desirable fermentation may be achieved by adding little or a small amount of source of protein such as peptone or yeast extract used in a general microorganism culture medium. In this microbial fermentation process, monosaccharide is converted to metabolite quickly by microorganisms, as well as even starch or cellulose, hemicellulose that is not saccharified in the previous enzymatic hydrolysis process as a result of feedback inhibition phenomenon of monosaccharide produced by saccharification of starch or cellulose and hemicellulose and remains in the pretreatment product, and then converted to microbial metabolite.

In the present disclosure, by the principle as described above, although the liquid hot water pretreatment condition of lignocellulosic biomass containing starch is limited to the temperature and the reaction time in which an amount of hemicellulose sugar, i.e., xylose and galactose, arabinose and mannose, produced by enzymatic hydrolysis using the entire pretreatment product after liquid hot water pretreatment is at maximum, the yield of microbial metabolite obtained by subsequent enzymatic hydrolysis and microbial fermentation will be very high. In ordinary cases, if liquid hot water pretreatment of biomass is performed under this condition, a conversion rate of cellulose to glucose by subsequent enzymatic hydrolysis is very low. Thus, to overcome this, subsequent process is needed to increase enzymatic hydrolysis efficiency, and it includes that solid fraction is only used as substrate for enzymatic hydrolysis after removal of liquid containing many enzyme inhibitors by solid-liquid separation of the pretreatment product, or mechanical refining of the solid fraction prior to enzymatic hydrolysis. However, the present disclosure is intended to provide a method for producing microbial metabolite at high yields without this process.

In the method of treating lignocellulosic biomass containing starch according to the present disclosure, saccharification and fermentation of the biomass pretreatment product may be simultaneously performed by incorporation of step 2 and step 3. This simultaneous saccharification and co-fermentation is not greatly different from ordinary simultaneous saccharification and co-fermentation of biomass, and its method is not particularly limited. However, when considering a metabolite production rate and conversion efficiency, microbial fermentation may be performed at a slight time interval after the initiation of enzymatic hydrolysis of the pretreatment product. The time interval is from 1 minute to 24 hours, and preferably about 2 hours.

In the method of treating lignocellulosic biomass containing starch according to the present disclosure, the principal feature is that the liquid hot water pretreatment condition in which the yield of hemicellulose sugar is at maximum is used for pretreatment of biomass, enzymes are added to the entire pretreatment product to perform saccharification, and the entire saccharification product is used as a source of carbon for microbial fermentation. When the liquid hot water pretreatment condition in which the yield of hemicellulose sugar is at maximum is used for pretreatment of biomass, a conversion rate to glucose by subsequent enzymatic hydrolysis is low, but the entire saccharification product can be used in microbial fermentation without detoxification process. Also, as glucose is converted to metabolite by microorganisms in the subsequent fermentation process, the glucose concentration is reduced, and the activity of cellulose hydrolysis enzyme suppressed by feedback inhibition is recovered, which makes it possible to convert still remaining portion of cellulose and hemicellulose in the pretreatment product into monosaccharide, and as a result, a conversion rate of biomass to microbial metabolite will be maximized.

In the method of efficiently producing microbial metabolite from lignocellulosic biomass containing starch according to the present disclosure, the step 1 of the method 2 is a step of adding boiling water or steam to lignocellulosic biomass containing starch to gelatinize starch and swelling biomass to perform sterilization. In this instance, boiling water or steam should be added in a sufficient amount for thoroughly wetting biomass. Thus, a ratio of biomass and water is preferably from 1:3 to 1:20, and when considering flowability of wet biomass to be easily handled, uniform mixing for subsequent liquid hot water pretreatment, and a recovery cost of metabolite after fermentation using microorganisms, 1:5 to 1:15 is more desirable.

The step 2 of the method 2 is a step of adding starch hydrolase to the biomass suspension in which starch is gelatinized, to hydrolyze the starch, and the method such as described in the description of the term may be used. To prevent unwanted contamination by microorganisms in advance, the reaction time at this starch hydrolysis step is preferably limited within 24 hours, and because an amount of starch hydrolytic enzyme can be changed depending on an amount of starch contained in biomass, its amount is not particularly limited, but approximately from 3 to 30 μL may be used per 1 g starch.

The step 3 of the method 2 is a step of inoculating the suspension containing starch hydrolysate with microorganisms to perform fermentation. At this step, most of glucose produced by hydrolysis of starch can be fermented to relatively chemically stable microbial metabolite at high temperature such as ethanol or buthanol. This conversion of starch to microbial metabolite prior to subsequent liquid hot water pretreatment has not only an effect of removing starch estimated as acting as an obstruction to a hydrolysis reaction of hemicellulose in subsequent liquid hot water pretreatment, but also an effect of reducing the initial concentration of glucose acting as a feedback inhibitor of enzymes in the enzymatic hydrolysis after liquid hot water pretreatment, thereby maximizing the yield of final microbial metabolite. The microorganism inoculated to convert glucose to microbial metabolite at this step may be the same as or different from microorganisms to be used in the subsequent step 6, but is not particularly limited except the case where a material produced as a result of fermentation acts as acids in the step 4, thereby making liquid hot water pretreatment impossible, or it is harmful to microorganisms to be cultivated at the step 6. Also, because the biomass suspension containing the starch hydrolysate already contains a considerable amount of nutrients necessary for fermentation of microorganisms such as protein and inorganic salts, there is no particular need for an additive for creation of a culture medium at this step, but if necessary, it is desirable to limit the type and amount of the material within the range in which the material is not converted to toxic materials by subsequent liquid hot water pretreatment even though the material is added.

In the method of efficiently producing microbial metabolite from lignocellulosic biomass containing starch according to the present disclosure, the steps 4, 5 and 6 of the method 2 are not greatly different from the steps 1, 2 and 3 of the method 1.

Also, in the method of efficiently producing microbial metabolite from lignocellulosic biomass containing starch according to the present disclosure, saccharification and fermentation of the gelatinized starch by enzymes could be simultaneously performed by incorporation of steps 2 and 3 of the method 2. This simultaneous saccharification and co-fermentation is not greatly different from ordinary simultaneous saccharification and co-fermentation of biomass, and its method is not particularly limited. However, when considering a metabolite production rate and conversion efficiency, microbial fermentation may be performed at a slight time interval after the initiation of saccharification of starch by enzymes. The time interval is from 1 minute to 24 hours, and preferably about 2 hours.

In the method of treating lignocellulosic biomass containing starch according to the present disclosure, saccharification and fermentation of the biomass pretreatment product could be simultaneously performed by incorporation of steps 5 and 6 of the method 2. This simultaneous saccharification and co-fermentation is not greatly different from ordinary simultaneous saccharification and co-fermentation of biomass, and its method is not particularly limited. However, when considering a metabolite production rate and conversion efficiency, microbial fermentation may be performed at a slight time interval after the initiation of enzymatic hydrolysis of the pretreated product. The time interval is from 1 minute to 24 hours, and preferably about 2 hours.

In the method 2 of treating lignocellulosic biomass containing starch according to the present disclosure, the main feature is that starch contained in biomass is converted to glucose by enzymes and then produced glucose is fermented to microbial metabolite prior to liquid hot water pretreatment, so the efficiency of subsequent liquid hot water pretreatment, and enzymatic hydrolysis and microbial fermentation is maximized, and the yield of microbial metabolite is higher than the method 1 of treating lignocellulosic biomass containing starch according to the present disclosure.

Therefore, the method of efficiently producing microbial metabolite from lignocellulosic biomass containing starch according to the present disclosure may produce microbial metabolite at even higher yield than conventional pretreatment and saccharification technology.

<A Method for Preparing a Sugar Solution Using a Separation Membrane>

The present disclosure provides a method for preparing a sugar solution including the following steps:

1) modifying a polyamide nanofiltration membrane with sodium hypochlorite and polyethylene glycol methacrylate (step 1); and 2) filtering an aqueous sugar solution obtained by hydrolyzing cellulosic biomass using the modified polyamide nanofiltration membrane to recover a refined sugar solution from the non-permeate side and remove fermentation inhibitors from the permeate side (step 2).

The step 1 is a step of modifying a polyamide nanofiltration membrane with sodium hypochlorite and polyethylene glycol methacrylate, and refers to a step of modifying a polyamide nanofiltration membrane to reduce surface charge.

The term "polyamide nanofiltration membrane" as used herein represents a nanofiltration membrane in which a functional layer uses polyamide as a main ingredient.

The polyamide nanofiltration membrane available in the present disclosure may be an aromatic polyamide nanofiltration membrane made using meta-phenylene diamine as diamine and trimesoyl chloride as acid chloride.

For effective removal of fermentation inhibitors, the present disclosure is characterized in that the polyamide nanofiltration membrane is modified to reduce surface charge at the step 1) and is used in the subsequent filtration step.

In the present disclosure, the modification at the step 1) may be performed by dipping a polyamide nanofiltration membrane in an aqueous solution containing sodium hypochlorite and polyethylene glycol methacrylate.

In the present disclosure, the concentration of sodium hypochlorite is preferably from 0.5 to 3 wt %. If the concentration of sodium hypochlorite is lower than the lower limit, there are disadvantages in that the reactivity is too low and a modification effect is not great, and if the concentration of sodium hypochlorite is higher than the upper limit, there is a disadvantage in that the separation membrane is decomposed.

In the present disclosure, the concentration of polyethylene glycol methacrylate is preferably from 0.05 to 0.5 wt %. If the concentration of polyethylene glycol methacrylate is lower than the lower limit, there are disadvantages in that the degree of substitution is too low and a modification effect is reduced, and if the concentration of polyethylene glycol methacrylate is higher than the upper limit, a modification effect does not increase any longer, so the concentration does not need to be higher than the upper limit.

In the present disclosure, the dipping may be performed for 3 to 30 minutes.

The step 1-1 is a step of filtering an aqueous sugar solution obtained by hydrolyzing cellulosic biomass using a microfiltration membrane or ultrafiltration membrane to recover a sugar solution from the permeate side, and refers to a step of filtering out macromolecules or particles by filtering an aqueous sugar solution using a microfiltration membrane or ultrafiltration membrane before filtration using a nanofiltration membrane.

In the present disclosure, the microfiltration membrane or ultrafiltration membrane may be made using fluorine-based, cellulose-based, polysulfone-based, vinyl-based polymers, or combinations thereof.

The step 2 is a step of filtering an aqueous sugar solution obtained by hydrolyzing cellulosic biomass using the modified polyamide nanofiltration membrane and recovering a refined sugar solution from the non-permeate side and remove fermentation inhibitors from the permeate side, and refers to a step of filtering the aqueous sugar solution using the modified polyamide nanofiltration membrane and concentrating the sugar solution and removing fermentation inhibitors.

The term "cellulosic biomass" as used herein is lignocellulosic or herbaceous biomass, and represents biomass including polysaccharides cellulose that is a main substance of the cell walls.

The hydrolysis of cellulosic biomass may be performed through any known method, for example, a concentrated sulfuric acid method, a diluted sulfuric acid method, and an enzyme method. Specifically, hydrolysis of cellulosic biomass may be performed using the concentration of sulfuric acid of 2% (w/w) under the condition of temperature of 150~250° C., and pressure of about 1~2 MPa for 60 seconds~40 minutes.

In the present disclosure, the aqueous sugar solution obtained by hydrolyzing cellulosic biomass contains fermentation inhibitors, together with monosaccharide such as glucose or xylose. Also, in addition to them, the aqueous sugar solution may contain oligosaccharide, cellulose, and salt such as KCl.

The term "fermentation inhibitor" as used herein represents a material that inhibitively acts on the fermentation process using microorganisms, causing microbial growth inhibition and a reduction in yield of fermentation products. Thus, a subsequent fermentation process can be effectively performed after removing fermentation inhibitors in the preparation process of the sugar solution.

The fermentation inhibitors removable in the present disclosure may be at least one selected from the group consisting of organic acids, furan compounds, and phenol compounds. Specifically, organic acids include, for example, acetic acid or formic acid, and furan compounds include, for example, furfural and hydroxymethylfurfural.

The method of preparing a sugar solution according to the present disclosure is characterized in that the filtration at the step 2) is performed by a constant volume filtration method to efficiently remove fermentation inhibitors. That is, fermentation inhibitors are removed by adding water as much as permeated out.

In the present disclosure, the pH of the aqueous sugar solution at the step 2) may be from 4 to 8.

In the present disclosure, the temperature of the aqueous sugar solution at the step 2) may be from 15 to 40° C.

The step 2-1 is a step of filtering the refined sugar solution filtered by a microfiltration membrane or ultrafiltration membrane using a reverse osmosis membrane to recover a refined sugar solution from the non-permeate side and remove fermentation inhibitors from the permeate side, and refers to a step of filtering, using a reverse osmosis membrane, the sugar solution previously refined using a nanofiltration membrane and further concentrating the sugar solution and additionally removing fermentation inhibitors.

The reverse osmosis membrane available in the present disclosure may be an aromatic polyamide reverse osmosis membrane made using meta-phenylene diamine as diamine and trimesoyl chloride as acid chloride.

In the present disclosure, a reverse osmosis membrane having reduced anionic surface charge is preferable. A reverse osmosis membrane for seawater desalination or low pressure reverse osmosis membrane having relatively high surface charge is not used.

For effective removal of fermentation inhibitors, the present disclosure may use a reverse osmosis membrane modified to further reduce the surface charge.

In the present disclosure, the modification of the reverse osmosis membrane may be performed by dipping the reverse osmosis membrane in an aqueous solution containing sodium hypochlorite and polyethylene glycol methacrylate.

In the present disclosure, the concentration of sodium hypochlorite is preferably from 0.5 to 3 wt %. If the concentration of sodium hypochlorite is lower than the lower limit, there are disadvantages in that the reactivity is too low and a modification effect is not great, and if the concentration of sodium hypochlorite is higher than the upper limit, there is a disadvantage in that the separation membrane is decomposed.

In the present disclosure, the concentration of polyethylene glycol methacrylate is preferably from 0.05 to 0.5 wt %. If the concentration of polyethylene glycol methacrylate is lower than the lower limit, there are disadvantages in that the degree of substitution is too low and a modification effect is reduced, and if the concentration of polyethylene glycol methacrylate is higher than the upper limit, a modification effect does not increase any longer, so the concentration does not need to be higher than the upper limit.

In the present disclosure, the dipping may be performed for 3 to 30 minutes.

In the present disclosure, the filtration at the step 2-1) may be performed by a constant volume filtration method to efficiently remove fermentation inhibitor. That is, fermentation inhibitors are removed by adding water as much as permeated out.

Because the reverse osmosis membrane used in the present disclosure has reduced anionic surface by modification to reduce surface charge, there is no need to adjust the pH of the aqueous sugar solution to an acid pH to separate fermentation inhibitors, in particular, organic acids such as acetic acid and formic acid. In the present disclosure, the pH of the aqueous sugar solution at the step 2-1) may be from 6 to 9.

In the present disclosure, the temperature of the aqueous sugar solution at the step 2-1) may be from 15 to 40° C.

Hereinafter, the present disclosure will be described in more detail based on the examples. The following examples are provided for illustration only, and the scope of the present disclosure is not limited thereto.

Example 1: Production of Fermentable Sugar Using Sunflower Stalks as a Raw Material Sunflower stalks powder of a known ingredient composition was weighed at 360 g of dry weight and put into a cotton cloth bag, and the cotton cloth bag was put into a 95° C. steamer containing 3,600 g distilled water and heated for 10 minutes. Subsequently, the cotton cloth bag was put into a centrifugal dehydrator to dehydrate it. After dehydration, the cotton cloth bag was put into a 95° C. steamer containing 2,400 g distilled water to be allowed to absorb enough water, and after removed, was dehydrated by a centrifugal dehydrator. The contents in the cotton cloth bag were divided into three and put into a 2 L reactor (Parr reactor; Parr Instrument Co. Ltd., USA) jar, and distilled water was added so that the contents weighed 1,500 g respectively. Liquid hot water pretreatment was performed by heating the reactor at 190° C. for 5 minutes. After the reaction finished, the reactor jar was cooled quickly by dipping it in running water, and the contents were transferred to a cotton cloth bag. The above process was repeated 5 times more, and a total of 720 g biomass was pretreated and then all collected, put into a cotton cloth bag, and dehydrated by a centrifugal dehydrator. The dehydrated pretreated solid was transferred to a fermentor jar of a fermenter (BioTron, Republic of Korea), and de-ionized water was added to reach 4 kg in total. 72 g diatomite powder (RexM, Pohang, Republic of Korea) was added thereto and stirred. Subsequently, 64.8 mL Cellic CTec2 and 7.2 mL Cellic HTec2 was added as cellulose hydrolysis enzyme, and stirred at 150 rpm while maintaining a fermentor at 50±1° C. and pH 5.0±0.1. Saccharification is completed in 3 days after the start of saccharification to prepare an undiluted sugar solution, an amount of saccharification products was measured, and 1 mL sample was harvested and used as a sample for composition analysis. The saccharification product in the fermentor jar was transferred to a cotton cloth bag and dehydrated by a centrifugal dehydrator to recover a sugar solution. The cotton cloth bag having undergone recovery once was put into a beaker containing 800 mL distilled water to be allowed to absorb water, kept cool for 12 hours or longer, and dehydrated again to separate the sugar solution. This process was repeated 2 times more, and the sugar solution was collected and mixed with the undiluted sugar solution. This sugar solution was heated at 121° C. for 20 minutes to denature and precipitate an enzyme, centrifugal separation, and filtration with a filter paper to obtain a clean sugar solution. Subsequently, the sugar solution was put into a membrane concentrator (self-production) with a reverse osmosis membrane module (RE1812-80, Woongjin, Republic of Korea), and concentration was carried out to prepare a sugar solution having a glucose concentration of 300 g/L or more (hereinafter referred to as 'fermentable sugar 1').

The fermentable sugar was analyzed by Waters HPLC BioRad Aminex HPX-87H column and refractive index detector, and the concentration of glucose and other sugars and acetic acid was calculated and the yield was calculated by conversion therefrom. The concentration of furfural and HMF was measured, and the yield of the sugar solution before concentration was shown in the following Table 2 and the concentration of fermentable sugar after concentration was shown in the following Table 3. Also, with a phenolic material produced by extraction from the sunflower stalks pretreatment product as a reference material, fermentable sugar was diluted 200 times, absorbance was measured at 320 nm by a spectrophotometer (Beckmann, Germany), and the calculated concentration of the phenolic material in the sugar solution was shown in Table 3. The content of inorganic salts in the high concentration of fermentable sugar was measured by Plasma-Atomic Emission Spectrometer (ICP-AES, Thermo Scientific, USA), and each material was indicated in total.

Comparative Example 1: Sugar Solution Prepared by Washing the Pretreatment Solid after Liquid Hot Water Treatment of Sunflower Stalks The sunflower stalks powder used in Example 1 was weighed at 120 g of dry weight and put into a jar of a 2 L reactor (Parr reactor; Parr Instrument Co. Ltd., USA), and distilled water was added so that the contents weighed 1,500 g respectively. Subsequently, liquid hot water pretreatment of the mixture was performed at 190° C. for 5 minutes. After the reaction finished, the reactor jar was cooled quickly by dipping it in running water, and the contents were transferred to a cotton cloth bag. The above process was repeated 5 times more, and a total of 720 g biomass was pretreated and then all collected, put into a cotton cloth bag, and dehydrated by a centrifugal dehydrator. The dehydrated solid was soaked in 20 L boiling water and dehydrated by a centrifugal dehydrator. The dehydrated pretreated solid was transferred to a fermentor jar of a fermenter (BioTron, Republic of Korea), and de-ionized water was added to reach 4 kg in total. 72 g diatomite powder was added thereto and stirred. Subsequently, the fermentor jar was sealed and put into an autoclave to sterilize at 121° C. for 60 minutes. 64.8 mL Cellic CTec2 and 7.2 mL Cellic HTec2 as cellulose hydrolysis enzyme were dissolved in de-ionized water 430 mL, was filtered by a filter system (Corning, USA) with a 0.22 μm membrane filter, and was put into the fermentor jar within a clean bench. Stirring was performed at 150 rpm while maintaining the fermentor at 50±1° C. and pH 5.0±0.1. To investigate whether lactic acid bacteria as one of the main microorganisms contaminating sugar solution occurred, saccharification products were collected at a time interval of 1 day while stirring for 3 days after enzymatic hydrolysis initiation, the yield of glucose and other sugars, and lactic acid and acetic acid was calculated by Waters HPLC with BioRad Aminex HPX-87H column and refractive index detector, and the concentration of furfural and HMF was measured and its result was shown in the following Table 2. The saccharification product in the fermentor jar was transferred to a cotton cloth bag and dehydrated by a centrifugal dehydrator to recover a sugar solution. The cotton cloth bag having undergone recovery once was put into a beaker containing 800 mL distilled water to be allowed to absorb water, kept cool for 12 hours or more, and dehydrated again to separate the sugar solution. This manipulation was repeated 2 times more, and the sugar solution was collected and mixed with the undiluted sugar solution. This sugar solution was heated at 121° C. for 20 minutes to denature and precipitate an enzyme, centrifugal separation, and filtration with a filter paper to obtain a clean sugar solution. The sugar solution was put into a membrane concentrator (self-production) with a reverse osmosis membrane module, and concentration was carried out to produce a fermentable sugar having a glucose concentration of 300 g/L or more (hereinafter referred to as 'fermentable sugar 2').

This sugar solution was analyzed by HPLC, and the concentration of each material including sugar was measured and its result was shown in Table 3. Also, the concentration of phenolic materials and inorganic salts was measured by the same method as Example 1 and its result was shown in Table 3.

Comparative Example 2: Production of Fermentable Sugar Using Sunflower Stalks of which Extractable Materials were not Removed as a Raw Material The sunflower stalks powder used in Example 1 was weighed at 120 g of dry weight and put into a jar of a 2 L reactor (Parr reactor; Parr Instrument Co. Ltd., USA), and distilled water was added so that the contents weighed 1,500 g respectively. Subsequently, liquid hot water pretreatment of the mixture was performed at 190° C. for 5 minutes. After the reaction finished, the reactor jar was cooled quickly by dipping it in running water, and the contents were transferred to a cotton cloth bag. The above process was repeated 5 times more, and a total of 720 g biomass was pretreated and then all collected, put into a cotton cloth bag, and dehydrated by a centrifugal dehydrator. The dehydrated pretreated solid was transferred to a fermentor jar of a fermentor (BioTron, Republic of Korea), and de-ionized water was added to reach 4 kg in total. 72 g diatomite powder was added thereto and stirred. Subsequently, 64.8 mL Cellic CTec2 and 7.2 mL Cellic HTec2 as cellulose hydrolysis enzyme was added, and stirring was performed at 150 rpm while maintaining the fermentor at 50±1° C. and pH 5.0±0.1. Saccharification was completed by stirring for 3 days after enzymatic hydrolysis initiation to prepare an undiluted sugar solution, and 1 ml sample was taken and used for composition analysis. The undiluted sugar solution was analyzed by Waters HPLC with BioRad Aminex HPX-87H column and refractive index detector to calculate the yield of glucose and other sugars and acetic acid, and the concentration of furfural and HMF was measured and its result was shown in the following Table 2. The saccharification product in the fermentor jar was transferred to a cotton cloth bag and dehydrated by a centrifugal dehydrator to recover a sugar solution. The cotton cloth bag having undergone recovery once was put into a beaker containing 800 mL distilled water to be allowed to absorb water, kept cool for 12 hours or longer, and dehydrated again to separate the sugar solution. This manipulation was repeated 2 times more, and the sugar solution was collected and mixed with the undiluted sugar solution. This sugar solution was heated at 121° C. for 20 minutes to denature and precipitate an enzyme, centrifugal separation, and filtration with a filter paper to obtain a clean sugar solution. The sugar solution was put into a concentrator (self-production) with a reverse osmosis membrane module, and concentration was carried out to produce a fermentable sugar having a glucose concentration of 300 g/L or more (hereinafter referred to as 'fermentable sugar 3').

This sugar solution was analyzed by HPLC, and the concentration of each material including sugar was measured and its result was shown in Table 3. Also, the concentration of phenolic materials and inorganic salts was measured by the same method as Example 1 and its result was shown in Table 3.

The processes of producing fermentable sugar according to Example 1, Comparative example 1 and Comparative example 2 were summarized as shown in the following Table 1.

TABLE 1

|  | Example 1 | Comparative example 1 | Comparative example 2 |
|---|---|---|---|
| Removal of extractable material from raw material biomass using hot water extraction | dehydrating after heating at 95° C. for 10 min (twice in total) | — | — |
| Liquid hot water pretreatment | treating at 190° C. for 5 min | treating at 190° C. for 5 min | treating at 190° C. for 5 min |
| Treatment of pretreatment product | partially removing liquid by dehydration after cooling | hot water washing of the pretreated solid after cooling | partially removing liquid by dehydration after cooling |
| Sterilization of pretreatment product | — | at 121° C. for 60 min | — |
| Enzyme removal using filtration | — | 0.22 μm membrane filtration | — |
| Enzymatic hydrolysis of solid | 50 ± 1° C., pH 5.0 ± 0.1, 150 rpm | 50 ± 1° C., pH 5.0 ± 0.1, 150 rpm | 50 ± 1° C., pH 5.0 ± 0.1, 150 rpm |
| Enzyme removal | filtering after heating at 121° C. for 20 min | filtering after heating at 121° C. for 20 min | filtering after heating at 121° C. for 20 min |
| Concentration | reverse osmosis membrane module | reverse osmosis membrane module | reverse osmosis membrane module |

TABLE 2

| | Yield (g/100 g) and output | | |
|---|---|---|---|
| Material name | Example 1 | Comparative example 1 | Comparative example 2 |
| glucose | 29.6 | 26.3 | 30.3 |
| other sugars | 8.5 | 6.9 | 9.8 |
| acetic acid | 1.3 | 1.0 | 1.1 |
| lactic acid | 0.0 | 0.1 | 0.0 |
| HMF | 0.01 | 0.00 | 0.02 |
| furfural | 0.02 | 0.00 | 0.02 |

In the sunflower stalks used as biomass in this experiment, cellulose is 35.1 g (converted to glucose), hemicellulose is 18.8 g (converted to monosaccharide), and acetic acid is 4.5 g. As can be seen from the above Table 1, the sugar solution of Example 1 prepared by the method of producing bioethanol according to the present disclosure continued enzymatic hydrolysis without contamination by lactic acid bacteria up to 72 hours so that the glucose yield amounted to 29.6 g, and there was almost no production of further degraded products of sugars. Also, a small amount of liquid containing microbial inhibitors produced as a result of pretreatment is reserved in the pretreated solid and is introduced into enzymatic hydrolysis, and thus, the sugar yield may be increased by saccharification without contamination by lactic acid bacteria and with no need for sterilization.

In contrast, Comparative example 1, in which enzymatic hydrolysis was performed after washing the pretreated solid with hot water, started producing lactic acid in 24 hours after saccharification, and afterwards, the concentration sharply increased after 48 hours. Thus, enzymatic hydrolysis was stopped after 48 hours. The reason why the glucose yield of Comparative example 1 is significantly lower than the sugar solution of Example 1 of the present disclosure is in part because the enzymatic hydrolysis time was shorter, but in part because a portion of the pretreatment product was lost as fine particles during washing the pretreatment product with hot water. Washing with hot water to remove further degraded products of sugars and lignin degradation products contained in the pretreatment product is one method of increasing the purity of a sugar solution prepared by enzymatic hydrolysis, but it is difficult to avoid microbial contamination by lactic acid bacteria or the like during enzymatic hydrolysis, and it can be seen that it becomes a big obstruction of industrial production of fermentable sugar.

Also, the sugar yield of Comparative example 2 obtained by enzymatic hydrolysis of the solid obtained through solid-liquid separation of the pretreatment product of biomass was high as much as 30.3 g, but because raw biomass was used for pretreatment without hot water extraction, free sugar contained in biomass is included in the sugar solution. However, because this free sugar is susceptible to overdecomposition, as can be seen from the above Table 2, production of HMF and furfural is unavoidable. These overdecomposed products may be a factor that causes a chromatography process cost to increase during subsequent separation and purification of the sugar solution because they are impurities which must be removed to produce fermentable sugar with high concentration that can be widely applied to many microorganisms.

TABLE 3

| | Composition of high concentration of fermentable sugar for test (%) | | |
|---|---|---|---|
| Material name | fermentable sugar 1 | fermentable sugar 2 | fermentable sugar 3 |
| glucose | 30.0 | 30.1 | 30.5 |
| other sugars | 8.7 | 7.2 | 9.1 |

TABLE 3-continued

| | Composition of high concentration of fermentable sugar for test (%) | | |
|---|---|---|---|
| Material name | fermentable sugar 1 | fermentable sugar 2 | fermentable sugar 3 |
| acetic acid | 0.6 | 0.5 | 0.4 |
| lactic acid | 0.0 | 0.1 | 0.0 |
| HMF | 0.03 | 0.01 | 0.02 |
| furfural | 0.02 | 0.00 | 0.01 |
| phenolic material | 0.72 | 0.31 | 0.58 |
| inorganic salt | 0.31 | 0.16 | 0.82 |

The composition of fermentable sugar produced by concentrating a sugar solution obtained by liquid hot water pretreatment and enzymatic hydrolysis of sunflower stalks using a membrane separation is as shown in Table 3. When the sugar solution was concenturated to around 30%, the fermentable sugar 1 of the present disclosure and fermentable sugar 3 of Comparative example 2 contains a very small amount of HMF and furfural, but the fermentable sugar 2 obtained by enzymatic hydrolysis after washing the pretreatment product with hot water hardly contain such materials. There is no big difference in concentration of phenolic materials between the fermentable sugar 1 of the present disclosure and the fermentable sugar 3 of Comparative example 2, so it is found that this material is produced as a result of pretreatment. The fermentable sugar 2 of Comparative example 1, in which the pretreatment product was washed with hot water, also contains phenolic materials, which is because phenolic materials are released in the sugar solution during enzymatic hydrolysis even after its washing with hot water, showing the limited washing effect.

A proper concentration of impurities contained in the pretreatment product acts as an inhibitor of lactic acid bacteria together with the enzymatic hydrolysis temperature around 50° C., and the fermentable sugar 2 in which the concentration of HMF, furfural and phenolic materials is very low due to washing of the pretreatment product with hot water is vulnerable to contamination by lactic acid bacteria during enzymatic hydrolysis, and thus contains lactic acid after enzymatic hydrolysis.

One of the most distinguishing features seen from Table 3 is the content of inorganic salts, and the fermentable sugar 3 having omitted hot water extraction of raw biomass has the content of inorganic salts higher about 2.6 times or more than the fermentable sugar 1 of the present disclosure in which 90% of extractable materials was removed by hot water extraction of biomass. This concentration of inorganic salts is at a very high level as compared to the concentration of inorganic salts added when cultivating industrial microbes, and it is predictable that growth can be inhibited according to the type of microorganisms.

Comparative Example 3: Comparison to Fermentable Sugar Produced by Removing Extractable Materials by Continuous Fractionation Method The method of the present disclosure was compared to a method of removing extractable materials by continuous fractionation disclosed in Korean Patent Publication No. 2011-0040367.

Prior Art Korean Patent Publication No. 2011-0040367 discloses, in Example 2 and Test example 1, a method by which hot water extractable materials are removed by continuous fractionation, and fermentable sugar is produced by liquid hot water pretreatment and enzymatic hydrolysis, and discloses a sugar yield. The sugar yield of fermentable sugar obtained from the prior art was xylose 10.1 g and glucose 28.2 g per 100 g dry weight of sunflower stalks respectively. This was total sugar yield resulting from saccharification of the pretreated liquid and solid obtained after pretreatment.

In contrast, in Example 1 of the present disclosure, the sugar yield of the sugar solution obtained by enzymatic hydrolysis of the pretreated solid containing liquid within the range of 30% after pretreatment of the same biomass as the prior art was xylose 8.5 g and glucose 29.6 g. When the above xylose yield from the pretreated solid is added to 7.5 g xylose obtained by enzymatic hydrolysis of liquid which can be fractionated by centrifugal separation of pretreatment product, total xylose yield amount to 16.0 g, so it can be seen that the method of the present disclosure is much better in terms of sugar yield than the prior art. This is because liquid recovery was imperfect when hemicellulose was hydrolyzed from sunflower stalks using continuous fractionation equipment, and the produced liquid was recovered through a valve. That is, a large amount of hemicellulose hydrolysate is contained in subsequent pretreatment and xylose is lost due to further degradation at high temperature that is why sugar yield was low. Also, a further degraded product, furfural, is thereby produced in large amounts, so in the case where fermentable sugar is produced by the prior art, it is predicted that a high cost for purification will be added.

When considering this result, it can be seen that the method of the prior art using biomass continuous fractionation equipment is not too effective in completely recovering liquid after high temperature reaction. In contrast, the present disclosure may produce fermentable sugar by the most economical method by effectively fractionating biomass using effective solid-liquid separation technology such as centrifugal separation after hot water extraction or pretreatment of biomass.

Test Example 1

Fermentation Strain Growth Test Using Fermentable Sugar of the Present Disclosure as a Nutrient Cultivation test of fermentation strain was conducted using fermentable sugar 1, 2 and 3 of Example 1 and Comparative examples 1 and 2. First, *E. coli* XB, *Lactobacillus paracasei* 13169 and *Clostridium beijerinckii* N8052 (pKBE4112ADH) were cultivated on each of 2 mL LB, MRS and 2YTG culture medium to produce seeds. Subsequently, culture media were prepared on P2, MR and LAB culture medium using each of fermentable sugar 1, 2 and 3 of Example 1 and Comparative examples 1 and 2 instead of glucose. Specifically, P2 culture medium was prepared by adding 20 g/L fermentable sugar, 5 g/L yeast extract, vitamins 1.5-fold, inorganic salts 1.5-fold and a buffer solution 1.5-fold; MR culture medium was prepared by adding 20 g/L fermentable sugar, 6.67 g/L $KH_2PO_4$, 4 g/L $(NH_4)_2HPO_4$, 0.8 g/L citric acid and trace metals in 5 ml/L aqueous solution containing a small amount of each of iron sulfate, calcium chloride, zinc sulfate, manganese sulfate, copper sulfate, molybdate and borate; LAB culture medium was prepared by adding 20 g/L fermentable sugar, 5 g/L polypeptone, 5 g/L yeast extract, 0.1 g/L sodium chloride and 0.5 g/L $MgSO_4$. Subsequently, each culture medium was inoculated with 0.2% seed, to cultivate *E. coli* XB and *Lactobacillus paracasei* 13169 under aerobic conditions and Clostridium beijerinckii N8052 (pKBE4112ADH) under anaerobic conditions at 37±1° C. During cultivation, samples were collected at a predetermined time (24, 48, 72 and 92 hours) interval and the degree of microorganism growth was determined by measuring optical density. The test was each conducted twice repetitively and resulting values were averaged. Each culture medium was produced using glucose for a reagent to prepare a control, and of which fermentation test was conducted by the same method and its result was shown in Tables 4 to 6.

TABLE 4

| | Optical density change of E. coli XB culture fluid | | | |
|---|---|---|---|---|
| Cultivation time | glucose control | fermentable sugar 1 | fermentable sugar 2 | fermentable sugar 3 |
| 0 | 0.05 | 0.39 | 0.37 | 0.63 |
| 24 | 2.30 | 2.69 | 1.98 | 0.63 |
| 48 | 2.21 | 3.47 | 2.82 | 1.28 |
| 72 | 2.33 | 3.63 | 3.01 | 1.91 |
| 96 | 2.36 | — | 3.28 | 2.03 |

TABLE 5

| | Optical density change of Lactobacillus paracasei 13169 culture fluid | | | |
|---|---|---|---|---|
| Cultivation time | glucose control | fermentable sugar 1 | fermentable sugar 2 | fermentable sugar 3 |
| 0 | 0.20 | 0.46 | 0.55 | 0.48 |
| 24 | 2.23 | 5.87 | 6.54 | 6.35 |
| 48 | 2.54 | 6.88 | 7.50 | 6.86 |
| 72 | 2.70 | 7.09 | 7.86 | 6.57 |
| 96 | 2.80 | — | — | 7.77 |

TABLE 6

| | Optical density change of Clostridium beijerinckii N8052 culture fluid | | | |
|---|---|---|---|---|
| Cultivation time | control | fermentable sugar 1 | fermentable sugar 2 | fermentable sugar 3 |
| 0 | 0.03 | 0.26 | 0.27 | 0.53 |
| 24 | 1.30 | 0.45 | 0.31 | 0.54 |
| 48 | 2.38 | 2.84 | 0.34 | 1.29 |
| 72 | 3.50 | 3.03 | 0.34 | 2.87 |
| 96 | 3.31 | — | 0.34 | 3.13 |

As can be seen from the above Table 4, *E. coli* XB showed better growth on fermentable sugar 1 than the control using glucose as carbon source. *E. coli* XB was grown better even on fermentable sugar 2 containing a small amount of lactic acid than that of the control but showed slightly poorer growth than fermentable sugar 1, and the growth on fermentable sugar 3 containing inorganic salts and impurities was poorer than that of the control.

On the other hand, as can be seen from Table 5, *Lactobacillus paracasei* 13169 was grown relatively well on all the fermentable sugar and was least sensitive to impurities.

In contrast, as can be seen from Table 6, *Clostridium beijerinckii* N8052 was little grown on fermentable sugar 2 containing a small amount of lactic acid, and showed almost equivalent growth on fermentable sugar 1 to the control. Also, a growth rate of fermentable sugar 3 containing a largest amount of inorganic salts was slightly lower than that of fermentable sugar 1 of the present disclosure.

Test Example 2

Production of Bioethanol Using Fermentable Sugar of the Present Disclosure

Alcohol fermentation was performed using fermentable sugar 1, 2 and 3 of Example 1 and Comparative examples 1 and 2. First, *Saccharomyce cerevisiae* was cultivated on 40 ml YPD liquid culture medium (10 g/L yeast extract, 20 g/L peptone and 50 g/L glucose) to produce seeds.

Subsequently, a control culture medium using glucose as a carbon source and fermentable sugar 1, 2 and 3 culture media using fermentable sugar as a carbon source were prepared respectively. Specifically, the control culture medium was prepared by adding 60 g/L glucose, 10 g/L yeast extract and 20 g/L peptone, and the fermentable sugar 1, 2 and 3 culture media were prepared by adding 60 g/L fermentable sugar instead of glucose, under the same preparation condition as that of the control culture medium. Subsequently, each culture medium was inoculated with 7% seed, and cultivated at 30±1° C. under anaerobic conditions. During cultivation, samples were collected at a predetermined time (6, 12, 24, 48 and 72 hours) interval and analyzed by Waters HPLC with BioRad Aminex HPX-87H column and refractive index detector to measure the ethanol concentration. The test was each conducted three times repetitively and results were averaged and shown in Table 7.

TABLE 7

| | Ethanol yield change (g/L) of culture fluid inoculated with ethanologen | | | |
|---|---|---|---|---|
| Cultivation time (hour) | glucose control | fermentable sugar 1 | fermentable sugar 2 | fermentable sugar 3 |
| 0 | 0.10 | 0.31 | 0.23 | 0.40 |
| 6 | 2.83 | 1.76 | 1.96 | 1.75 |
| 12 | 27.8 | 20.5 | 23.7 | 19.5 |
| 24 | 28.3 | 31.2 | 30.7 | 31.5 |
| 48 | 28.1 | 30.8 | 30.6 | 31.5 |
| 72 | 28.4 | 30.3 | 30.2 | 30.9 |

As can be seen from the above Table 7, all the fermentable sugar of fermentable sugar 1, 2 and 3 had a higher amount of ethanol produced than the control using glucose as a carbon source. Particularly, an amount of ethanol produced from fermentable sugar 1, 2 and 3 was higher in 24 hours after cultivation initiation at which an amount of ethanol produced from the control was highest. As can be seen from Table 3, it is found that fermentable sugar 1 of the present disclosure does not affect the growth of strains or production of ethanol as a fermentation product because it contains not only acetic acid which can be usefully used as a carbon source of ethanologen, but also sugar other than glucose derived from biomass such as xylose. Thus, it can be seen that the fermentable sugar of the present disclosure is suitable for ethanol fermentation more than glucose for a reagent.

Example 2: Production of Fermentable Sugar Using Sunflower Stalks as a Raw Material Sunflower stalks powder of a known ingredient composition was weighed at 120 g of dry weight on a scale and put into a 2 L high pressure reactor (Parr reactor; Parr Instrument Co. Ltd., USA) jar, and distilled water was added so that the contents weighed 1,500 g. Liquid hot water pretreatment was performed at 190° C. for 5 minutes. After the reaction finished, the reactor jar was cooled quickly by dipping it in running water, and the pretreatment product were transferred to a cotton cloth bag. It was put into a centrifugal dehydrator (Chalsney®, Hanil Electric, Republic of Korea) to conduct dehydration for 30 minutes. The dehydrated solid in the cotton cloth bag was put into a plastic bag which was then sealed, and was put into an autoclave set to temperature: 90° C. and time: 30 minutes. 2.04 g calcium hydroxide was put into a beaker (5 L) which 1,200 ml distilled water was added to, it was put into a 90° C. constant temperature water bath (10 L, Daihan Scientific, Republic of Korea) and heated. Before the set time of the autoclave is over and cooling starts, the autoclaved pretreatment product in the cotton cloth bag was taken out, and the opening of the cotton cloth bag was opened and added to the beaker containing the aqueous calcium hydroxide solution (pH 12.7) in the constant temperature water bath set to 90° C. and agitated for 3 minutes. The pretreatment product was all taken out and transferred to a cotton cloth bag again, and dehydrated for 5 minutes to remove the aqueous calcium hydroxide solution. The dehydrated pretreatment product in the cotton cloth bag was soaked in a 5 L beaker containing 1.2 L distilled water to be allowed to absorb water, and resting for 1 hour and this soaking and dehydration step was repeated three times to remove calcium hydroxide. The solid remaining in the cotton cloth bag was transferred to a fermentor jar of a 5 L fermenter (BioTron, Republic of Korea), and de-inonized water was added to reach 740 g in total. Subsequently, the fermentor jar was sealed and put into the autoclave, followed by sterilization at 121° C. for 60 minutes. 12 ml Cellic CTec2 as cellulose hydrolysis enzyme was dissolved in 108 mL de-ionized water, filtered by a filter system (Corning, USA) with a 0.22 µm membrane filter, and put into the fermentor jar placed in a clean bench. Enzymatic hydrolysis was carried out with stirring at 150 rpm while maintaining the fermentor at 50±1° C. and pH 5.0±0.1 for 72 hours. A portion of the hydrolysate was taken and subjected to centrifugal separation to obtain a supernatant, and after conducting an analysis by Waters HPLC with BioRad Aminex HPX-87H column and refractive index detector, the yield of glucose and other sugars and acetic acid was calculated and shown in the following Table 8.

Example 3: Production of Fermentable Sugar Using Reed as a Raw Material

The powdered Korean native reed of a known ingredient composition was weighed at 150 g of dry weight and put into a 2 L high pressure reactor (Parr reactor; Parr Instrument Co. Ltd., USA) jar, and distilled water was added so that the contents weighed 1,500 g. Liquid hot water pretreatment was performed at 200° C. for 10 minutes by heating the reactor. After the reaction finished, the reactor jar was cooled quickly by dipping it in running water, and the pretreatment product was transferred to a cotton cloth bag. It was put into a centrifugal dehydrator (Chalsney®, Hanil Electric, Republic of Korea) to conduct dehydration for 30 minutes. The dehydrated solid in the cotton cloth bag was put into a plastic bag which was then sealed, and was put into an autoclave set to temperature: 90° C. and time: 30 minutes. 5.56 g calcium hydroxide was put into a constant temperature water bath (10 L, Daihan Scientific, Republic of Korea) which 900 ml distilled water was added to and heat to reach 90° C. Before the set time of the autoclave is over and cooling starts, the the autoclaved pretreatment product in the cotton cloth bag was taken out, and the opening of the cotton cloth bag was opened and the contents were added to the beaker containing the aqueous calcium hydroxide solution (pH 12.7) in the constant temperature water tank and agitated for 3 minutes. The contents were all taken out and transferred to a cotton cloth bag again, and dehydrated for 5 minutes to remove the aqueous calcium hydroxide solution. The dehydrated pretreatment product in the cotton cloth bag was soaked in a 5 L beaker containing 1.2 L distilled water to be allowed to absorb water, and resting for 1 hour and this soaking and dehydration step was repeated three times to remove calcium hydroxide. The solid remaining in the cotton cloth bag was transferred to a fermentor jar of a 5 L fermenter (BioTron, Republic of Korea), and de-ionized water was added to reach 950 g in total. Subsequently, the fermentor jar was sealed and put into the autoclave, followed by sterilization at 121° C. for 60 minutes. 13.5 ml Cellic CTec2 and 1.5 ml Cellic HTec2 as cellulose hydrolysis enzyme was dissolved in 135 ml de-ionized water, filtered by a filter system (Corning, USA) with a 0.22 µm membrane filter, and put into the fermentor jar placed in a clean bench. Enzymatic hydrolysis was carried out with stirring at 150 rpm while maintaining the fermentor at 50±1° C. and pH 5.0±0.1 for 72 hours. A portion of the hydrolysate was taken and subjected to centrifugal separation to obtain a supernatant, and after conducting an analysis by Waters HPLC with BioRad Aminex HPX-87H column and refractive index detector, the yield of glucose and other sugars and acetic acid was calculated and shown in the following Table 8.

Comparative Example 4: Sugar Solution Prepared by Washing Liquid Hot Water Pretreatment Product of Sunflower Stalks as a Raw Biomass Sunflower stalks powder used in Example 2 was weighed at 120 g of dry weight and put into a jar of a 2 L reactor (Parr reactor; Parr Instrument Co. Ltd., USA), and distilled water was added so that the contents weighed 1,500 g. Subsequently, liquid hot water pretreatment of the mixture was performed at 190° C. for 5 minutes. After the reaction finished, the reactor jar was cooled quickly by dipping it in running water, and the contents were transferred to a cotton cloth bag. It was put into a centrifugal dehydrator (Chalsney®, Hanil Electric, Republic of Korea) to conduct dehydration for 30 minutes. The dehydrated solid was soaked in 20 L boiling water and dehydrated by a centrifugal dehydrator. Subsequently, it was soaked in 20 L room temperature water and dehydrated again. The solid remaining in the cotton cloth bag was transferred to a fermentor jar of a 5 L fermenter (BioTron, Republic of Korea), and de-ionized water was added to reach 740 g in total. Subsequently, the fermentor jar was sealed and put into an autoclave to sterilize at 121° C. for 60 minutes. 24 ml Cellic CTec2 as cellulose hydrolysis enzyme was dissolved in 96 mL de-ionized water, filtered by a filter system (Corning, USA) with a 0.22 µm membrane filter, and put into the fermentor jar placed in a clean bench. Enzymatic hydrolysis was carried out with stirring at 150 rpm while maintaining the fermentor at 50±1° C. and pH 5.0±0.1 for 72 hours. A portion of the hydrolysate was taken and subjected to centrifugal separation to obtain a supernatant, and after conducting an analysis by Waters HPLC with BioRad Aminex HPX-87H column and refractive index detector, the yield of glucose and other sugars and acetic acid was calculated and shown in the following Table 8.

Comparative Example 5: Production of Fermentable Sugar Using Reed as a Raw Material The powdered Korean native reed of a known ingredient composition was weighed at 150 g of dry weight and put into a 2 L high pressure reactor (Parr reactor; Parr Instrument Co. Ltd., USA) jar, and distilled water was added so that the contents weighed 1,500 g. Liquid hot water pretreatment was performed at 200° C. for 10 minutes by heating the reactor. After the reaction finished, the reactor jar was cooled quickly by dipping it in running water, and the contents were transferred to a cotton cloth bag. It was put into a centrifugal dehydrator (Chalsney®, Hanil Electric, Republic of Korea) to conduct dehydration for 30 minutes. The dehydrated solid was soaked in a 20 L boiling water and dehydrated by a centrifugal dehydrator. Subsequently, it was soaked in 20 L room temperature water and dehydrated again. The solid remaining in the cotton cloth bag was transferred to a fermentor jar of a 5 L fermenter (BioTron, Republic of Korea), and de-ionized water was added to reach 950 g in total. Subsequently, the fermentor jar was sealed and put into an autoclave to sterilize at 121° C. for 60 minutes. 13.5 ml Cellic CTec2 and 1.5 ml Cellic HTec2 as cellulose hydrolysis enzyme was dissolved in 135 ml ultrapure water, filtered by a filter system (from Corning, USA) with a 0.22 µm membrane filter, and put into the fermentor jar placed in a clean bench. Enzymatic hydrolysis was carried out with stirring at 150 rpm while maintaining the fermentor at 50±1° C. and pH 5.0±0.1 for 72 hours. A portion of the hydrolysate was taken and subjected to centrifugal separation to obtain a supernatant, and after conducting an analysis by Waters HPLC with BioRad Aminex HPX-87H column and refractive index detector, the yield of glucose and other sugars and acetic acid was calculated and shown in the following Table 8.

TABLE 8

| | Yield (g/100 g biomass) | | | |
| | Sunflower stalks | | Reed | |
| Material name | Example 2 | Comparative example 4 | Example 3 | Comparative example 5 |
|---|---|---|---|---|
| glucose | 27.0 | 24.2 | 34.8 | 34.2 |
| other sugars | 4.5 | 4.5 | 1.7 | 1.6 |
| acetic acid | 0.09 | 0.51 | 0.05 | 0.25 |
| HMF | 0.0 | 0.00 | 0.0 | 0.0 |
| furfural | 0.0 | 0.00 | 0.0 | 0.0 |

As can be seen from the above Table 8, the acetic acid yield by a method which washes the liquid hot water pretreatment product of the present disclosure with the aqueous alkali solution to remove acetic acid is 0.09 g per 100 g biomass in Example 2 using sunflower stalks as a raw material, which just corresponds to ⅕ of 0.51 g of Comparative example 4 obtained by enzymatic hydrolysis after simply washing with boiling water. Also, the acetic acid yield in Example 3 using reed as a raw material is 0.05 g per 100 g biomass, while the acetic acid yield in Comparative example 5 is 0.25 g, so the acetic acid yield in Example 3 just corresponds to ⅕ of the acetic acid yield of Comparative example 5. Thus, because the method of the present disclosure can greatly reduce the concentration of acetic acid in the sugar solution only by washing the liquid hot water pretreatment product of biomass with the aqueous alkali solution at temperature less than or equal to 100° C., the method of the present disclosure is very advantageous for production of fermentable sugar for microbial fermentation.

Also, the method of the present disclosure has an effect on an increased sugar yield as well as acetic acid removal when compared to a hot water washing method, and has no sugar loss during acetic acid removal.

Example 4: Preparation of Calcium Hydroxide Suspension for pH Adjustment 10 g calcium hydroxide (first-grade reagent, Dong Yang Chemical, Republic of Korea) powder was added to 90 g de-ionized water. This was fed into a wet mill (Eiger motormill, Japan) including glass beads having an average diameter of 2 mm, and was ground at 3500 rpm for 20 minutes to prepare a colloidal suspension having an average diameter of about 0.8 µm. The concentration of calcium hydroxide in the prepared suspension was 10% (w/w), and the suspension was used as an alkali reagent for pH adjustment when performing enzymatic hydrolysis of a biomass pretreatment product.

Example 5: Production of Fermentable Sugar Using Sunflower Stalks as a Raw Material Sunflower stalks powder of a known ingredient composition was weighed at 480 g of dry weight on a scale and put into a cotton cloth bag and the bag was sealed. Two samples, each containing 480 g of biomass, were prepared and put into a bucket containing 19 L boiling water for 10 minutes. It was put into a centrifugal dehydrator (Chalsney®, Hanil Electric, Republic of Korea) to conduct dehydration for 30 minutes. The samples were taken out and weighed to calculate an amount of raw material samples equivalent to 120 g. The amount of raw material samples equivalent to 120 g was put into a 2 L high pressure reactor (Parr reactor; Parr Instrument Co. Ltd., USA) jar and distilled water was added so that the contents weighed 1,500 g. Liquid hot water pretreatment was performed at 180° C. for 25 minutes by heating the reactor.

After the reaction finished, the reactor jar was cooled quickly by dipping it in running water, and the contents were transferred to a fermentor jar of 5 L fermenter (BioTron, Republic of Korea). 12 ml Cellic CTec2 as a cellulose hydrolysis enzyme was added to the fermentor jar and enzymatic hydrolysis was carried out for 72 hours with stirring at 150 rpm while maintaining 50±1° C. and pH 5.0±0.1. In this instance, the calcium hydroxide suspension (10%, w/w %) prepared in Example 4 as an alkali reagent for pH adjustment was automatically fed to maintain the saccharification system at pH 5.0. After the obtained hydrolysate was transferred to a 500 ml centrifugal tube and undergone centrifugal separation (Combi-514R, Hanil Scientific, Republic of Korea) at 4300 rpm for 1 hour to obtain a supernatant, this sugar solution was concentrated by a membrane concentrator with a reverse osmosis membrane module (BWRO, Woongjin Chemical, Republic of Korea) to remove only water, yielding fermentable sugar containing 240 g/L glucose. After this fermentable sugar was analyzed by Waters HPLC with BioRad Aminex HPX-87H column and refractive index detector, the concentration of glucose and other sugars and acetic acid was calculated and shown in the following Table 9.

Comparative Example 6: Production Fermentable Sugar with Sunflower Stalks as a Raw Biomass Using an Aqueous Sodium Hydroxide Solution as a Neutralizing Agent It was performed by the same method as Example 5 except that an aqueous sodium hydroxide solution (4%, w/w %) was used as an alkali reagent for pH adjustment of an enzymatic hydrolysate. The concentration of glucose and other sugars and acetic acid in the obtained sugar solution was calculated and shown in the following Table 9.

TABLE 9

| Material | Concentration (g/1000 g) | |
| --- | --- | --- |
| name | Example 5 | Comparative example 6 |
| glucose | 240 | 241 |
| other sugars | 147 | 147 |
| acetic acid | 39 | 40 |
| HMF | 0 | 0 |
| furfural | 0 | 0 |

As can be seen from the above Table 9, it is found by a chemical analysis method that the method of the present disclosure using a calcium hydroxide suspension as an alkali reagent for pH adjustment does not reduce in the concentration of acetic acid acting as a microbial growth inhibitor as compared to a general method using an aqueous sodium hydroxide solution. However, it can be seen from the test example 3 that even though their concentrations of acetic acid are similar, the concentrations of acetic acid biologically affecting microbial fermentation are markedly different.

Test Example 3

Alcohol Fermentation Using Yeast

Alcohol fermentation was performed using fermentable sugar and glucose for a reagent (Sigma-Aldrich Korea) obtained in Example 5 and Comparative example 6.

First, *Saccharomyce cerevisiae* was cultivated on 40 ml YPD liquid culture medium (10 g/L yeast extract, 20 g/L peptone and 50 g/L glucose) using fermentable sugar of Example 5 and Comparative example 6 to produce a seed. Subsequently, the control culture media 1 and 2 respectively using glucose for a reagent and fermentable sugar of Comparative example 6 as a carbon source and culture medium of Example 5 using fermentable sugar of Example 5 as a carbon source were prepared respectively. Specifically, the control culture medium 1 was prepared by adding 120 g/L glucose for a reagent, 20 g/L yeast extract and 40 g/L peptone, and each of the control culture medium 2 and the culture medium of Example 5 was prepared using 120 g/L fermentable sugar of Comparative example 6 and 120 g/L fermentable sugar of Example 5, instead of glucose for a reagent, by the same preparation method as the control culture medium 1. Subsequently, each culture medium was inoculated with 7% seed, and cultivated at 30±1° C. under anaerobic conditions. During cultivation, samples were collected at a predetermined time (6, 12, 24, 48 and 72 hours) interval and analyzed by Waters HPLC with BioRad Aminex HPX-87H column and refractive index detector to measure the ethanol concentration. The test was each conducted three times repetitively and results were averaged and shown in Table 10.

TABLE 10

| | Ethanol yield change (g/L) of culture fluid inoculated with ethanologen | | |
| --- | --- | --- | --- |
| Cultivation time (hour) | Control culture medium 1 (glucose for a reagent) | Control culture medium 2 (sodium hydroxide neutralization) | Culture medium of Example 5 (calcium hydroxide neutralization) |
| 0 | 0.22 | 0.16 | 0.18 |
| 9 | 34.7 | 0.35 | 11.8 |
| 12 | 56.5 | 0.59 | 38.0 |
| 18 | 56.9 | 2.70 | 58.8 |
| 24 | 56.8 | 16.3 | 58.0 |

As can be seen from the above Table 10, because the control culture medium 2 contains 20 g/L acetic acid neutralized with the aqueous sodium hydroxide solution, the growth of yeast is greatly inhibited and an amount of ethanol produced is very low.

In contrast, although fermentable sugar of Example 5 neutralized with the calcium hydroxide suspension in the enzymatic hydrolysis process of the sunflower pretreatment product contains acetic acid of the same concentration as the control culture medium 2, it shows a similar level of ethanol yield to the control culture medium 1 containing no acetic acid. This is because acetic acid ion ($CH_3COO^-$) produced by first dissociation of calcium diacetate ($CH_3COO$—Ca—$OOCCH_3$) is in such form that affects the growth of yeast, but its concentration is not as much high as doing harm, and the remaining $CH_3COO$—$Ca^+$ does not dissociate under weak acidic to neutral or higher conditions and does not act as acid.

Example 6: Production of Bioethanol from Biomass by Method 1

Oil palm trunk [Korindo Group, Indonesia, composition per 100 g of dry weight: glucan 53.6 g (enzymatically hydrolyzable starch 26.9 g, cellulose 26.6 g), xylan 15.4 g, arabinan 2.4 g, acetyl group 3.4 g, ash 5.3 g] ground to 20 meshes or less using a food mill (Jalman grinder, Daehwa Precision, Republic of Korea) was weighed at 120 g of dry weight and put into a reaction tank of a high pressure reactor (Parr reactor, Parr Instrument Co., USA), and distilled water was added so that the contents weighed 1,500 g. The mixture was subjected to liquid hot water pretreatment at 180° C. for 30 minutes to produce a liquid hot water pretreatment product. Subsequently, the pretreatment product was cooled quickly at room temperature, and all transferred to a fermenter (Model LiFlus GX, BIOTRON, Republic of Korea), 10.8 ml Cellic CTec2, 1.2 ml Cellic HTec2 and 0.6 ml Novozyme 188 (all commercially available from Novozymes) as cellulose hydrolysis enzyme was added, and saccharification was performed for 24 hours while maintaining the fermentor at 50° C. and pH 5.0 to produce a saccharification product. On the other hand, *Saccharomyce cerevisiae* ATCC 24858 was pre-cultivated on a 40 ml YPD liquid culture medium (5 g/L yeast extract; 10 g/L peptone; 25 g/L glucose) to produce a seed. Subsequently, the seed was cultivated on the same YPD liquid culture medium again, and the saccharification product was inoculated with 5% seed to perform alcohol fermentation at 30±1° C. under anaerobic conditions. In 24 hours after cultivation, a sample was taken and analyzed by Waters HPLC with BioRad Aminex HPX-87H column and refractive index detector to measure the concentration of ethanol produced. As a result of calculating a real ethanol yield by comparing the yield calculated from the ethanol concentration to a theoretical ethanol yield (total glucan×0.51) calculated from the total glucan in the palm trunk, the total yield of ethanol amounted to 81.4%.

When considering 76.9%, 68.9% and 78.3% for each maximum ethanol yield reported in Document 1 [Chin et al, 2010, Optimization study of ethanolic fermentation from oil palm trunk, rubberwood, and mixed hardwood hydrolysates using *Saccharomyces cerevisiae, Bioresour. Technol.*, 101, 3287-3291] disclosing a method which prepares a sugar solution from ground palm trunk by concentrated sulfuric acid pretreatment, concentrated sulfuric acid hydrolysis and solid-liquid separation, followed by ethanol fermentation by yeast, Document 2 [Prawitwong et al, 2012, Efficient ethanol production from separated parenchyma and vascular bundle of oil palm trunk, *Bioresour. Technol.*, 125, 37-42] disclosing technology that obtains a sugar solution through alkali pretreatment and enzymatic hydrolysis after separating parenchyma and vascular bundles from palm trunks squeezed into sap vascular bundle and converts it to ethanol, and Document 3 [Jung et al, 2011, Ethanol production from oil palm trunks treated aqueous ammonia and cellulase, *Bioresour. Technol.*, 102, 7307-7312] disclosing technology that pretreats palm trunks with an ammonia solution, performs solid-liquid separation of the pretreatment product, performs enzymatic hydrolysis of only a solid to obtain a sugar solution, followed by ethanol fermentation, it can be seen that the bioethanol yield may be remarkably increased through the method of the present disclosure which uses whole palm trunk as a raw material without pre-fractionation treatment for each tissue of the palm trunk and performs enzymatic hydrolysis and fermentation of the entire pretreatment product after pretreatment without solid-liquid separation.

Example 7: Production of Lactic Acid from Biomass by Method 1

Oil palm trunk [Korindo Group, Indonesia, composition per 100 g of dry weight: glucan 56.1 g (enzymatically hydrolyzable starch 31.0 g, cellulose 25.1 g), xylan 18.4 g, arabinan 4.1 g, acetyl group 3.3 g] ground to 20 meshes or less using a food mill (Jalman grinder, Daehwa Precision, Republic of Korea) was weighed at 120 g of dry weight and put into a reactor jar of a high pressure reactor (Parr reactor, Parr Instrument Co., USA), and distilled water was added so that the contents weighed 1,500 g. The contents were subjected to liquid hot water pretreatment at 180° C. for 30 minutes to produce a liquid hot water pretreatment product. Subsequently, the pretreatment product was cooled quickly at room temperature, and all transferred to a fermenter (Model LiFlus GX, BIOTRON, Republic of Korea), 10.8 ml Cellic CTec2, 1.2 ml Cellic HTec2 and 0.6 ml Novozyme 188 (all commercially available from Novozymes) as cellulose hydrolysis enzyme was added, and saccharification was performed for 24 hours while maintaining the fermentor at 50° C. and pH 5.0 to produce a saccharification product. Subsequently, the saccharification product was sterilized at 121° C. for 20 minutes to prepare a culture medium for alcohol fermentation. On the other hand, the saccharification product was inoculated with 0.2% seed obtained by cultivating *Lactobacillus paracasei* KCTC 13169 on 2 mL MRS culture medium, and lactic acid fermentation was performed at 37±1° C. under aerobic conditions. In 48 hours after cultivation, a sample was taken and analyzed by Waters HPLC with BioRad Aminex HPX-87H column and refractive index detector to measure the concentration of lactic acid produced. As a result of calculating a real lactic acid yield by comparing the yield calculated from the lactic acid concentration to a theoretical lactic acid yield calculated form the total glucan included in the palm trunk, the total yield of lactic acid amounted to 98.5%.

Example 8: Production of Bioethanol from Biomass by Method 2

Oil palm trunk [Korindo Group, Indonesia, composition per 100 g of dry weight: glucan 53.6 g (enzymatically hydrolyzable starch 26.9 g, cellulose 26.6 g), xylan 15.4 g, arabinan 2.4 g, acetyl group 3.4 g, ash 5.3 g] ground to 20 meshes or less using a food mill
(Jalman grinder, Daehwa Precision, Republic of Korea) was weighed at 120 g of dry weight and put into a fermenter (Model LiFlus GX, BIOTRON, Republic of Korea), and 1,080 ml non-ionic water was added and mixed with it. The mixture was sterilized at 121° C. for 20 minutes, and 0.6 ml starch hydrolase [enzyme prepared by mixing glucoamylase (Sigma A7095) and alpha-amylase (Sigma A8220) at a ratio of 9:1 and filtered by 0.22 μm membrane filter] was added, followed by hydrolysis for 24 hours while stirring at 50° C. at 150 rpm. Subsequently, the hydrolysate was inoculated with 5% *Saccharomyce cerevisiae* ATCC 24858 seed of Example 6, followed by alcohol fermentation at 30±1° C. for 24 hours under anaerobic conditions.

Subsequently, the whole fermented solution was put into a reaction jar of a high pressure reactor (Parr reactor, Parr Instrument Co, USA), and distilled water was added such that the product weighed 1,500 g, followed by liquid hot water pretreatment, saccharification and alcohol fermentation in the same manner as Example 6. After alcohol fermentation, a sample was taken and analyzed by Waters HPLC with BioRad Aminex HPX-87H column and refractive index detector, to measure the concentration of ethanol produced. As a result of calculating an actual ethanol yield by comparing the yield calculated from the ethanol concentration to a theoretical ethanol yield (total glucan×0.51) calculated from the total glucan included in the palm trunk, the total yield of ethanol amounted 93.5%.

The result shows that the ethanol yield may be significantly improved by additionally performing starch hydrolysis and subsequent ethanol fermentation prior to liquid hot water pretreatment in the method 1.

Example 9

As a sugar solution before filtration, an aqueous solution containing glucose 5 wt %, acetic acid 0.1 wt %, furfural 0.01 wt % and hydroxymethyl furfural (HMF) 0.01 wt % was used. Modified NE 90 (Woongjin Chemical, Republic of Korea) was used as nanofiltration membrane. The modification of the nanofiltration membrane was performed as follows.

First, modification was performed by soaking NE 90 sheet (membrane area 30 cm$^2$) in an aqueous solution containing 1 wt % NaOCl and 0.1 wt % polyethylene glycol methacrylate for 10 minutes. Subsequently, the NE 90 sheet was used after the NE 90 was washed with water.

Subsequently, the sugar solution before filtration was filtered by the NE 90 modified as described above, so that a refined sugar solution was recovered from the non-permeate side and fermentation inhibitors were removed from the permeate side. In this instance, the pressure was 30 kgf/cm$^2$, and the feed temperature was 30° C. Also, pH of the sugar solution was 5. A removal percentage of each material was shown in the following Table 11.

Example 10

Fermentation inhibitors were separated by constant volume filtration using NE 90 modified by the same modification method as the modification method disclosed in Example 9. The driving condition was the same as Example 9. Specifically, 50% sugar solution was permeated, and after pure water as much as permeated amounts was filled, 50% was permeated again. This process was repeated twice more, and the concentration of concentrate ingredients was measured and its result was shown in the following Table 11.

Example 11

The same process as Example 9 was performed except that reverse osmosis membrane (RE4040-SR, Woongjin Chemical, Republic of Korea) modified by the same modification method as the modification method disclosed in Example 9 was used. Its result was shown in the following Table 11.

Example 12

The same process as Example 10 was performed except that a reverse osmosis membrane (RE4040-SR, Woongjin Chemical, Republic of Korea) modified by the same modification method as the modification method disclosed in Example 9 was used. Its result was shown in the following Table 11.

Example 13

50% sugar solution was permeated by the same method as Example 9, and the permeated solution was permeated again under the same driving condition as Example 9 using a reverse osmosis membrane (RE8040-FE, Woongjin Chemical, Republic of Korea) having a low negative surface charge. Its result was shown in the following Table 11.

Example 14

90% of solution permeated by the same method as Example 10 was permeated using reverse osmosis membrane (RE8040-FE, Woongjin Chemical, Republic of Korea) modified by the same modification method as the modification method disclosed in Example 9. Its result was shown in the following Table 11.

Example 15

After filtering out macromolecules and particles from sugar solution before filtration by ultrafiltration membrane (Hisep, Synopex Chemicore, Republic of Korea), Example 14 was repeated. Its result was shown in the following Table 11.

Comparative Example 7

The same process as Example 9 was performed except that NE 90 was used without modification. Its result was shown in the following Table 11.

Comparative Example 8

The same process as Example 9 was performed except that a reverse osmosis membrane for seawater desalination (RE4040-SR, Woongjin Chemical, Republic of Korea) was used. Its result was shown in the following Table 11.

Comparative Example 9

The same process as Example 9 was performed except that a low pressure reverse osmosis membrane (RE4040-BLN, Woongjin Chemical, Republic of Korea) was used. Its result was shown in the following Table 11.

TABLE 11

| Material | Residual (%) | | | | | | | | | |
| --- | --- | --- | --- | --- | --- | --- | --- | --- | --- | --- |
|  | Example 9 | Example 10 | Example 11 | Example 12 | Example 13 | Example 14 | Example 15 | Comparative example 7 | Comparative example 8 | Comparative example 9 |
| Glucose | 99.5 | 97.3 | 99.91 | 99.8 | 99.94 | 99.96 | 99.92 | 99.5 | 99.91 | 99.7 |
| Acetic acid | 40 | 12 | 85.1 | 75 | 52 | 26 | 12 | 50 | 92.3 | 73 |
| Furfural | 30 | 5 | 79.8 | 71 | 45 | 12 | 5 | 40 | 91 | 75 |
| HMF[1] | 79 | 49 | 97.3 | 92 | 85 | 28 | 13 | 82 | 99.3 | 91.9 |

[Note]
[1] Hydroxymethyl furfural

Through the results of the above Table 11, it can be seen that in the case where a sugar solution is filtered using a polyamide nanofiltration membrane modified according to the method of the present disclosure (Example 9), monosaccharides such as glucose are concentrated and fermentation inhibitors such as acetic acid, furural, and hydroxymethyl furfural are removed as compared to the where an unmodified polyamide nanofiltration membrane is used (Comparative example 7).

Also, it can be seen that in the case where filtration is performed using constant volume filtration (Examples 10 and 12), the removal percentage of fermentation inhibitors is further increased as compared to the case where constant volume filtration is not used although the same membrane is used (Examples 9 and 11).

Also, in the case where additional refining using a modified reverse osmosis membrane is performed after filtration using a modified polyamide nanofiltration membrane (Examples 14 and 15), monosaccharides are more concentrated as compared to the case where additional refining using a reverse osmosis membrane is not performed (Example 10).

Also, it can be seen that in the case where filtration using an ultrafiltration membrane is performed before filtration using a nanofiltration membrane and a reverse osmosis membrane (Example 15), the removal percentage of fermentation inhibitory substances is higher than the case where filtration using an ultrafiltration membrane is not performed (Example 14).

Finally, it can be seen that in the case of filtration using a reverse osmosis membrane for seawater desalination or a low pressure reverse osmosis membrane (Comparative examples 8 and 9), removal of fermentation inhibitors is difficult.

What is claimed is:

1. A method of producing fermentable sugar, the method comprising the steps of:

performing liquid hot water pretreatment of a lignocellulosic biomass at 160 to 230° C. temperature to produce a pretreatment product;

treating said pretreatment product with an aqueous alkali solution at pH 11 or higher and 80 to 105° C. temperature;

adjusting pH to 5.0+0.1 by adding a base having at least two hydroxyl groups, wherein the base is present in a form of an aqueous solution or a colloidal suspension having an average diameter of 0.001 to 10 μm, wherein the base forms a salt by neutralization reaction with acetic add produced by hydrolysis of the pretreatment product, and a dissolution constant ($pKa_2$) of a second acetyl group of the resulting salt is 8.0 or more;

contacting the pretreatment product after said adjusting with a cellulose hydrolyzing enzyme, and producing fermentable sugar solution having at least 9±1% acetic add by weight, relative to total sum of glucose, other sugars, acetic acid, 5-hydroxymethyl-2-furaldehyde (HMF), and furfural in the fermentable sugar solution.

2. The production method according to claim 1, wherein the pretreatment product used in the step of treating with an aqueous alkali solution is selected from the group consisting of:

a) both a liquid and solid obtained after performing the liquid hot water pretreatment of the lignocellulosic biomass;

b) a solid obtained by a solid-liquid separation step performed after the liquid hot water pretreatment of the lignocellulosic biomass; and c) a liquid pretreatment product obtained after performing the liquid hot water pretreatment of the lignocellulosic biomass.

3. The production method according to claim 1, wherein the liquid hot water pretreatment is performed at 160 to 230° C. for 1 to 60 minutes.

4. The production method according to claim 1, wherein the base is calcium hydroxide, barium hydroxide or magnesium hydroxide.

5. A method for fermentation comprising the steps of:

1) providing the fermentable sugar produced by the method according to claim 1; and 2) fermenting the fermentable sugar using at least one microorganism selected from the group consisting of: genus *Escherichia*, genus *Sacharomyces*, genus *Serratia*, genus *Lactobacillus*, genus *Lactococcus*, genus *Leuconostoc*, genus *Corynebacterium*, genus *Brevibacterium* or genus *Clostridium*.

6. The method according to claim 1, further comprising the step of:

maintaining pH at 5.0±0.1 and temperature at 50±1° C.

7. The method according to claim 4, wherein the base is calcium hydroxide.

8. The method according to claim 5, wherein the at least one microorganism is *Saccharomyces cerevisiae*.

* * * * *

UNITED STATES PATENT AND TRADEMARK OFFICE
CERTIFICATE OF CORRECTION

PATENT NO. : 10,329,589 B2
APPLICATION NO. : 14/991209
DATED : June 25, 2019
INVENTOR(S) : Ju Hyun Yu et al.

Page 1 of 1

It is certified that error appears in the above-identified patent and that said Letters Patent is hereby corrected as shown below:

On the Title Page

Column 1, Item (71), under Applicant, please amend the Applicant's name to read "Korea Research Institute of Chemical Technology".

In the Claims

Column 55, Line 23, please amend "acetic add" to read "acetic acid".

Column 55, Line 29, please amend "add by weight" to read "acid by weight".

Signed and Sealed this
Twenty-third Day of June, 2020

Andrei Iancu
*Director of the United States Patent and Trademark Office*